(12) United States Patent
Nguyen et al.

(10) Patent No.: US 7,473,267 B2
(45) Date of Patent: Jan. 6, 2009

(54) SYSTEM AND METHOD FOR MINIMALLY INVASIVE POSTERIOR FIXATION

(75) Inventors: Thanh V. Nguyen, Irvine, CA (US); Samuel M. Shaolian, Newport Beach, CA (US); George P. Teitelbaum, Santa Monica, CA (US); Michael R. Henson, Coto de Caza, CA (US); To V. Pham, Trabuco Canyon, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 834 days.

(21) Appl. No.: 10/462,098

(22) Filed: Jun. 13, 2003

(65) Prior Publication Data

US 2004/0215190 A1    Oct. 28, 2004

Related U.S. Application Data

(60) Provisional application No. 60/465,902, filed on Apr. 25, 2003.

(51) Int. Cl.
*A61B 17/88* (2006.01)
(52) U.S. Cl. .................................................. 606/279
(58) Field of Classification Search ............ 606/53, 606/60, 61, 96, 98, 99, 104, 103, 246, 264–270, 606/279
See application file for complete search history.

(56) References Cited

U.S. PATENT DOCUMENTS

| 2,338,159 | A | 1/1944 | Appleton |
|---|---|---|---|
| 4,041,939 | A | 8/1977 | Hall |
| 4,289,123 | A | 9/1981 | Dunn |
| 4,335,715 | A | 6/1982 | Kirkley |
| 4,648,388 | A | 3/1987 | Steffee |
| 4,653,481 | A | 3/1987 | Howland et al. |
| 4,657,533 | A | 4/1987 | Oscarsson |
| 4,722,331 | A | 2/1988 | Fox |
| 4,743,260 | A | 5/1988 | Burton |

(Continued)

FOREIGN PATENT DOCUMENTS

DE    197 26 754 A 1    2/1999

(Continued)

OTHER PUBLICATIONS

Muller et al., "A Keyhole Approach for Endoscopically Assisted Pedicle Screw Fixation in Lumbar Spine Instability". Neurosurgery, vol. 47, No. 1, Jul. 2000, pp. 85-96.

(Continued)

*Primary Examiner*—Eduardo C. Robert
*Assistant Examiner*—Michael J Araj
(74) *Attorney, Agent, or Firm*—Haynes and Boone, LLP

(57) ABSTRACT

The present invention relates generally to systems and methods for aligning and implanting orthopedic fixation or stabilization implants within the body. In one embodiment, the system includes at least two bone anchors, at least one of which is provided with an angularly adjustable connector. In one aspect, the system also includes at least one linkage rod, for linking two or more bone anchors through their respective adjustable connectors. The bone anchors and the linkage rod may be locked into place to form a spinal fusion or fixation prosthesis. An alignment tool is provided, for guiding a guidewire through one or more connectors.

21 Claims, 53 Drawing Sheets

U.S. PATENT DOCUMENTS

| | | | |
|---|---|---|---|
| 4,771,767 A | 9/1988 | Steffee | |
| 4,883,048 A | 11/1989 | Purnell et al. | |
| 4,887,595 A | 12/1989 | Heinig et al. | |
| 4,892,550 A | 1/1990 | Huebsch | |
| 4,920,958 A | 5/1990 | Walt et al. | |
| 4,957,495 A | 9/1990 | Kluger | |
| 4,998,936 A | 3/1991 | Mehdian | |
| 5,000,165 A | 3/1991 | Watanabe | |
| 5,030,220 A | 7/1991 | Howland | |
| 5,042,982 A | 8/1991 | Harms | |
| 5,084,049 A | 1/1992 | Asher et al. | |
| 5,084,051 A | 1/1992 | Törmälä et al. | |
| 5,112,337 A | 5/1992 | Paulos et al. | |
| 5,163,940 A | 11/1992 | Bourque | |
| 5,171,279 A | 12/1992 | Mathews | |
| 5,176,680 A | 1/1993 | Vignaud et al. | |
| 5,242,443 A | 9/1993 | Kambin | |
| 5,242,444 A | 9/1993 | MacMillan | |
| 5,281,223 A | 1/1994 | Ray | |
| 5,306,275 A | 4/1994 | Bryan | |
| 5,334,205 A | 8/1994 | Cain | |
| 5,342,361 A | 8/1994 | Yaun et al. | |
| 5,357,983 A | 10/1994 | Mathews | |
| 5,397,363 A | 3/1995 | Gelbarb | |
| 5,409,488 A | 4/1995 | Ulrich | |
| 5,464,407 A | 11/1995 | McGuire | |
| 5,474,551 A | 12/1995 | Finn et al. | |
| 5,484,418 A | 1/1996 | Quiachon et al. | |
| 5,486,174 A | 1/1996 | Fournet-Fayard et al. | |
| 5,496,322 A | 3/1996 | Mathews | |
| 5,520,689 A | 5/1996 | Schlapfer et al. | |
| 5,549,679 A | 8/1996 | Kuslich | |
| 5,562,661 A | 10/1996 | Yoshimi et al. | |
| 5,569,248 A | 10/1996 | Mathews | |
| 5,584,887 A | 12/1996 | Kambin | |
| 5,591,165 A | 1/1997 | Jackson | |
| 5,591,167 A | 1/1997 | Laurain et al. | |
| 5,613,971 A | 3/1997 | Lower et al. | |
| 5,643,273 A | 7/1997 | Clark | |
| 5,649,925 A | 7/1997 | Alacreu | |
| 5,658,286 A | 8/1997 | Sava | |
| 5,658,289 A | 8/1997 | Boucher | |
| 5,681,320 A | 10/1997 | McGuire | |
| 5,704,937 A | 1/1998 | Martin | |
| 5,728,097 A | 3/1998 | Mathews | |
| 5,728,112 A | 3/1998 | Yoon | |
| 5,733,260 A * | 3/1998 | DeMaio et al. | 604/164.13 |
| 5,752,955 A | 5/1998 | Errico | |
| 5,792,106 A | 8/1998 | Mische | |
| 5,800,435 A | 9/1998 | Errico et al. | |
| 5,840,059 A | 11/1998 | March et al. | |
| 5,879,713 A | 3/1999 | Roth et al. | |
| 5,891,150 A | 4/1999 | Chan | |
| 5,899,939 A | 5/1999 | Boyce et al. | |
| 5,910,142 A | 6/1999 | Tatar | |
| 5,938,663 A | 8/1999 | Petreto | |
| 5,961,516 A | 10/1999 | Graf | |
| 6,033,406 A | 3/2000 | Mathews | |
| 6,048,343 A | 4/2000 | Mathis et al. | |
| 6,099,528 A | 8/2000 | Saurat | |
| 6,102,912 A | 8/2000 | Cazin et al. | |
| 6,106,530 A | 8/2000 | Harada | |
| 6,120,511 A | 9/2000 | Chan | |
| 6,126,689 A | 10/2000 | Brett | |
| 6,127,597 A | 10/2000 | Beyar et al. | |
| 6,129,763 A | 10/2000 | Chauvin et al. | |
| 6,162,223 A | 12/2000 | Orsak et al. | |
| 6,175,758 B1 | 1/2001 | Kambin | |
| 6,187,011 B1 | 2/2001 | Torrie | |
| 6,206,922 B1 | 3/2001 | Zdeblick et al. | |
| 6,226,548 B1 | 5/2001 | Foley et al. | |
| 6,235,028 B1 | 5/2001 | Brumfield et al. | |
| 6,296,643 B1 * | 10/2001 | Hopf et al. | 606/61 |
| 6,296,644 B1 | 10/2001 | Saurat | |
| 6,336,930 B1 | 1/2002 | Stalcup et al. | |
| 6,402,784 B1 | 6/2002 | Wardlaw | |
| 6,425,923 B1 | 7/2002 | Stalcup et al. | |
| 6,530,926 B1 | 3/2003 | Davison | |
| 6,530,929 B1 * | 3/2003 | Justis et al. | 606/103 |
| 6,558,386 B1 | 5/2003 | Cragg | |
| 6,558,390 B2 | 5/2003 | Craig | |
| 6,582,467 B1 | 6/2003 | Teitelbaum et al. | |
| 6,726,691 B2 | 4/2004 | Osorio et al. | |
| 6,802,844 B2 | 10/2004 | Ferree | |
| 7,083,621 B2 | 8/2006 | Shaolian et al. | |
| 2002/0022764 A1 | 2/2002 | Smith et al. | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0082601 A1 | 6/2002 | Toyama et al. | |
| 2002/0143341 A1 | 10/2002 | Biedermann et al. | |
| 2002/0161368 A1 | 10/2002 | Foley et al. | |
| 2002/0198526 A1 | 12/2002 | Shaolian et al. | |
| 2003/0060826 A1 | 3/2003 | Foley et al. | |
| 2004/0006341 A1 | 1/2004 | Shaolian et al. | |
| 2004/0006344 A1 | 1/2004 | Nguyen et al. | |
| 2005/0010220 A1 * | 1/2005 | Casutt et al. | 606/61 |

FOREIGN PATENT DOCUMENTS

| | | |
|---|---|---|
| SU | 1 745 231 | 7/1992 |
| WO | WO 97/30666 | 8/1997 |
| WO | WO 97/38639 | 10/1997 |
| WO | WO 99/09902 | 3/1999 |
| WO | WO 99/15097 | 4/1999 |
| WO | WO 02/00126 A1 * | 1/2002 |

OTHER PUBLICATIONS

International Search report for Application No. PCT/US04/10902 ( the PCT counterpart of the parent application).

International Search report for European Application No. 00 98 9371 (The European counterpart of the parent application) mailed Jan. 2, 2007.

* cited by examiner

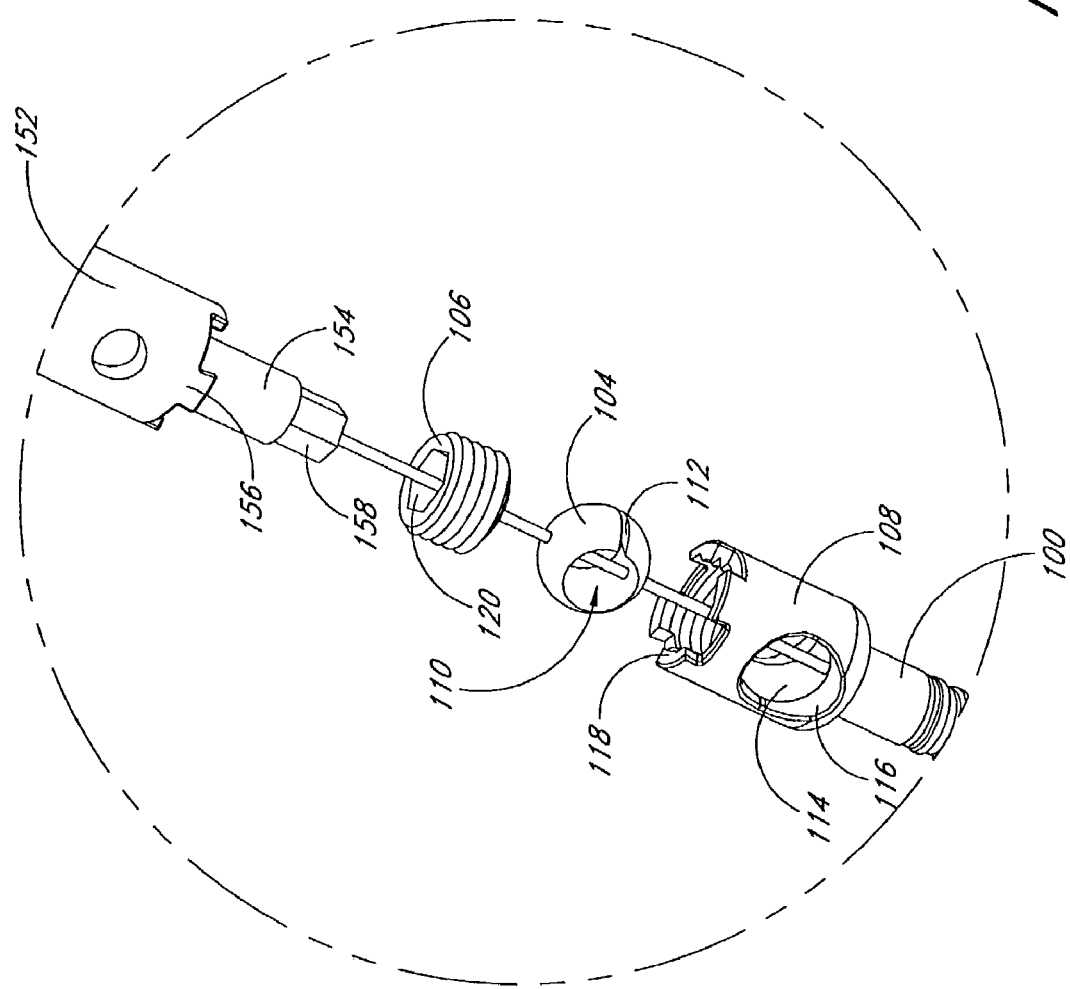

SYSTEM AND METHOD FOR MINIMALLY INVASIVE POSTERIOR FIXATION

RELATED APPLICATIONS

This application claims priority under 35 U.S.C. §119(e) to U.S. Provisional Application No. 60/465,902 filed on Apr. 25, 2003, the disclosure of which is incorporated by reference in its entirety herein.

BACKGROUND OF THE INVENTION

1. Field of the Invention

The present invention relates generally to medical devices and, more particularly, to systems for aligning and implanting orthopedic fixation or stabilization implants within the body. In one application, the present invention relates to minimally invasive procedures and devices for implanting posterior instrumentation.

2. Description of the Related Art

The human vertebrae and associated connective elements are subject to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to these diseases, conditions, injuries and manipulations often result from the displacement of all or part of a vertebra from the remainder of the vertebral column. A variety of methods have been developed to restore the displaced vertebrae or portions of displaced vertebrae to their normal position and to fix them within the vertebral column. For example, open reduction with screw fixation is one currently used method. The surgical procedure of attaching two or more parts of a bone with pins, screws, rods and plates requires an incision into the tissue surrounding the bone and the drilling of one or more holes through the bone parts to be joined. Due to the significant variation in bone size, configuration, and load requirements, a wide variety of bone fixation devices have been developed in the prior art. In general, the current standard of care relies upon a variety of metal wires, screws, rods, plates and clamps to stabilize the bone fragments during the healing or fusing process. These methods, however, are associated with a variety of disadvantages, such as morbidity, high costs, lengthy in-patient hospital stays and the pain associated with open procedures.

Therefore, devices and methods are needed for repositioning and fixing displaced vertebrae or portions of displaced vertebrae which cause less pain and potential complications. Preferably, the devices are implantable through a minimally invasive procedure.

SUMMARY OF THE INVENTION

In accordance with one aspect of the present invention, a system is provided for the minimally invasive implantation of posterior fixation hardware. The system generally includes at least two bone anchors, at least one of which is provided with an adjustable connector. In many clinical situations, all of the bone anchors used in the system may be provided with adjustable connectors. The system may also include a driver for inserting the bone anchor into a bone and locking the adjustable connector. The system also includes at least one linkage rod, for linking two or more bone anchors through their respective adjustable connectors. In one embodiment, an insertion tool is provided for the insertion of the linkage rod. The bone anchors and the linkage rod may be fixed to each other by the locking of the adjustable connectors on the bone anchors, to subcutaneously form a prosthesis.

In accordance with another aspect of the present invention, the system additionally includes a guidance apparatus for the minimally invasive implantation of posterior fixation hardware. In one embodiment, the guidance apparatus includes a central support arm adapted to engage a bone anchor. A radial arm is pivotably attached to the central arm. A hollow access needle is secured to the radial arm. The radial arm is pivotable with respect to the central arm, to allow the hollow access needle to travel along an arcuate path, for guiding a guidewire through a tissue tract and into and through at least one adjustable connector on a bone anchor (or bone screw). The hollow access needle may removably carry an obturator, to facilitate percutaneous advancement. The hollow needle may additionally removably carry a distal guidewire capture device, for capturing a proximally advancing guidewire subcutaneously within the hollow access needle. The guidewire capture device may comprise a radially enlargeable structure such as a conical funnel, for deflecting an approaching guidewire into the lumen of the hollow access needle.

In another aspect of the present invention, a method is provided for the minimally invasive implantation of posterior fixation hardware. In one embodiment, the method comprises the insertion of a first bone anchor, having a first adjustable connector, into a first vertebral body. A second bone anchor, having a second adjustable connector, is inserted into a second vertebral body. The first and second vertebral bodies may be adjacent to each other, or separated by one or more other vertebral body or bodies. A linkage rod is inserted through the adjustable connectors of both bone anchors. The adjustable connector of each bone anchor is then locked, fixing the position of the adjustable connector within the bone anchor, and securing the linkage rod within the adjustable connector, to form a prosthesis.

In accordance with another embodiment of the present invention, the method further comprises the insertion of another bone anchor with an adjustable connector into another vertebral body. This latter vertebral body may be adjacent to either or both of the first and second vertebral bodies, or separated from both the first and second vertebral bodies. The linkage rod is inserted through the adjustable connectors of all of the bone anchors to form the prosthesis.

In accordance with another embodiment of the present invention, the method additionally includes the placement of one or more guide wires. A guide wire may be inserted into a bone to define a path for the insertion of a bone anchor. Another guide wire may be threaded through the adjustable connectors of two or more bone anchors, to guide the insertion of the linkage rod. The guide wire may be placed using the guidance apparatus described above.

In any of the foregoing systems and methods, the guide wire may be replaced or supplemented by a flexible guide tube. In such implementations of the invention, the bone anchor and/or the linkage rod may be advanced through the interior of the guide tube.

Further features and advantages of the present invention will become apparent to those skilled in the art in view of the detailed description of preferred embodiments which follows, when considered together with the attached drawings.

BRIEF DESCRIPTION OF THE DRAWINGS

FIG. 3A is an enlarged view of the circled area in FIG. 2.

DETAILED DESCRIPTION OF THE PREFERRED EMBODIMENTS

Although the application of the present invention will be disclosed primarily in the context of a spinal fixation procedure, the systems and methods disclosed herein are intended for use in a wide variety of medical applications where the minimally invasive implantation of an attachment, bulking, brace, support, fixation or other prosthesis may be desirable.

One advantage of the prosthesis formation described in the various embodiments of the present invention is the ability to access a treatment site through minimally invasive pathways, while allowing the formation of a relatively larger prosthesis at the treatment site. In one embodiment, various components of a prosthesis are inserted into a patient through minimally invasive pathways, then joined to form a single prosthesis. This is facilitated by the angularly adjustable connectors between the various components, which provide leeway or angular adjustability as the components are joined. Afterwards, the junctions between the various components may be locked to fix or set the prosthesis in a desired configuration.

A corollary advantage of several embodiments is the ability to unlock and adjust one or more junctions between components of the prosthesis, to set the prosthesis in other desirable configurations during or even after its implantation and formation. The prosthesis may thus be adjusted in subsequent procedures.

The systems and methods for spinal fixation according to various embodiments of the present invention minimize procedure morbidity by avoiding open surgical cutdowns or other invasive access procedures. The basic percutaneous access, bone screw construction and implantation methods, and methods and structures for percutaneously positioning a fixation rod across bone screws, all of which are useful in the practice of the present invention, are disclosed in U.S. patent application Ser. No. 09/747,066, entitled Percutaneous Vertebral Fusion System, to Teitelbaum, filed Dec. 21, 2000; U.S. patent application Ser. No. 09/943,636 to Shaolian et al., entitled Formable Orthopedic Fixation System, filed Aug. 29, 2001; U.S. patent application Ser. No. 09/976,459 to Teitelbaum et al., entitled Formable Orthopedic Fixation System with Cross-Linking, filed Oct. 10, 2001; and U.S. patent application Ser. No. 10/161,554 to Shaolian et al., entitled Formed in Place Fixation System with Thermal Acceleration, filed May 31, 2002; the disclosures of all of which are hereby incorporated in their entireties by reference herein.

Figure 1:
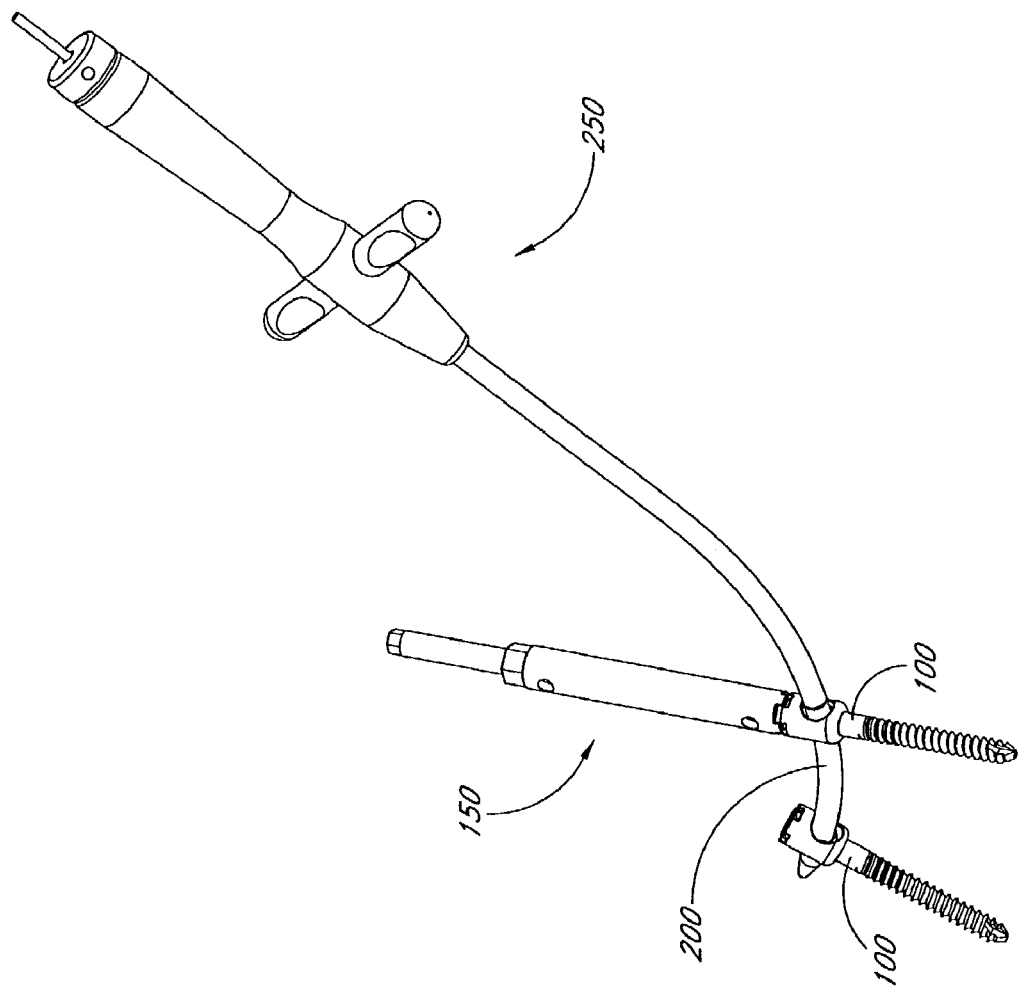
FIG. 1 is an overview of a system for minimally invasive posterior spinal fixation according to one embodiment of the present invention.

An overview of a system for minimally invasive posterior spinal fixation according to one embodiment of the present invention is provided in FIG. 1. The system includes at least two and optionally three or four or more bone anchors 100 and a linkage rod 200. In FIG. 1, the bone anchors are shown connected by the linkage rod 200. The system also includes a driver 150, shown engaging one of the bone anchors 100, and an insertion tool 250, shown connected to the linkage rod 200. Although the present invention will be described primarily in the context of a single linkage rod connected to two bone anchors, the normal fusion application will involve the implantation of two linkage rods, each carried by two or more bone anchors, bilaterally symmetrically mounted on the spine as is well understood in the art.

Figure 2:
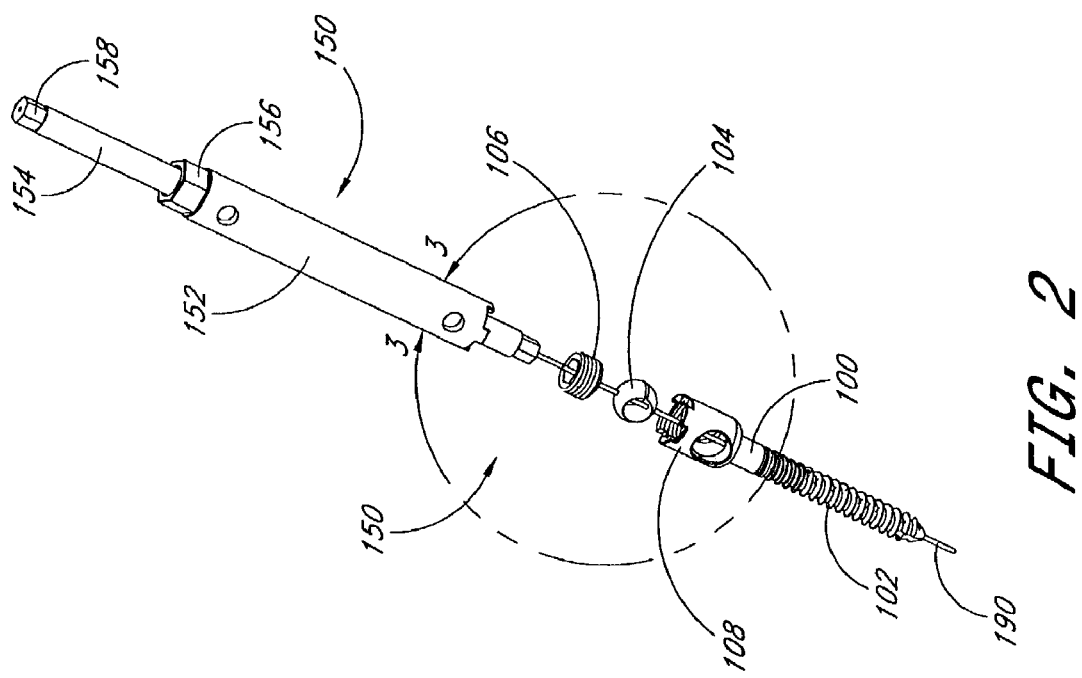
FIG. 2 is an exploded view of the bone anchor and the driver of FIG. 1.

FIG. 2 shows an exploded view of the bone anchor 100 and the driver 150. The bone anchor 100 is provided with threads 102 by which it is screwed into a vertebral body. A connector 104 and a locking cap 106 are disposed within the head 108 of the bone anchor 100.

The driver 150 comprises an outer adapter 152 concentrically arranged around an inner adapter 154. Either adapter may be freely rotated with respect to the other. The outer adapter 152 is adapted to engage the head 108, to screw the bone anchor 100 into a bone. The inner adapter 154 is adapted to engage the locking cap 106, to tighten the connector 104 within the head 108. In one embodiment, the hexagonal proximal end 156 of the outer adapter 152 allows torque to be applied to the outer adapter 152 by means of a wrench, a spanner or another tool. Similarly, the hexagonal proximal end 158 of the inner adapter 154 allows torque to be applied to the inner adapter 154.

Releasable, rotational engagement between the driver and the bone anchor may be accomplished in any of a variety of ways. In the illustrated embodiment, the distal end the inner adapter 154 is provided with at least one surface for cooperating with a complimentary surface on the proximal end of the bone anchor 100, for transmitting torque from the inner adapter 154 to the bone anchor 100, to enable transmission of torque from the inner adapter 154 to locking cap 106. Similarly, the distal end of the outer adapter 152 is provided with at least one surface for cooperating with a complimentary surface on the proximal end of the bone anchor 100, for transmitted torque from the outer adapter 152 to the bone anchor 100 to enable credible engagement between the bone anchor 100 and the vertebral body.

In one embodiment, the bone anchor 100, its connector 104, its locking cap 106, and the inner adapter 154 are all provided with a central axial lumen through which a guide wire 190 may pass.

FIG. 3A is an enlarged view of the circled area in FIG. 2, showing the proximal head 108 of the bone anchor 100 and the distal ends of the outer adapter 152 and the inner adapter 154. The connector 104 and the locking cap 106 are disposed within the head 108. In one embodiment, the connector 104 is spherical with an aperture 110 extending therethrough, and a gap 112 in its circumference, such that it is approximately C-shaped when viewed along the central axis of the aperture 110. The aperture 110 is adapted for the insertion of a linkage rod (not shown), and has a diameter slightly larger than that of the linkage rod. One skilled in the art will understand that the connector 104 can be provided in a variety of suitable shapes.

In one embodiment, the connector 104 is seated on a race or groove 114 within the head 108. The groove 114 is preferably provided with a complementary surface to the spherical exterior surface of the connector 104. The connector 104 may rotate on any axis within the head 108 of the bone anchor (or bone screw) 100. A locking cap 106 may be threaded into the head 108 to lock the connector 104 against the linkage rod 200, by compressing the groove 114, fixing the connector 104 within the head 108. The bottom of the locking cap 106 may be provided with a concave surface (not shown) which is complementary to the spherical exterior surface of the connector 104.

A transverse portal 116 extends through the head 108 along an axis approximately perpendicular to the central axis of the bone anchor 100. While the aperture 110 of the connector 104 and the transverse portal 116 of the head 108 are illustrated as circular, they may be of different shapes in other embodiments, depending upon the cross sectional shape of the fixation rod (e.g. oval, elliptical, rectangular, square, etc.). The diameter of the transverse portal 116 is generally smaller than the outside diameter of the uncompressed connector 104 but greater than the inside diameter of the aperture 110. Before the locking cap 106 is tightened, the connector 104 may rotate on any axis within the head 108 to accommodate different entrance angles for the fixation rod. Thus the central axis of the aperture 110 and the central axis of the transverse portal 116 may be coaxial or angularly offset.

In one embodiment, the threading of the locking cap 106 into the head 108 compresses the connector 104, decreasing the width of the gap 112 and reducing the cross sectional area of the aperture 110. This secures a linkage rod (not shown) extending through the transverse portal 116 of the bone anchor 100 within the aperture 110. The tightening of the locking cap 106 into the head 108 also fixes the rotational position of the connector 104 within the head 108.

Figure 3B:
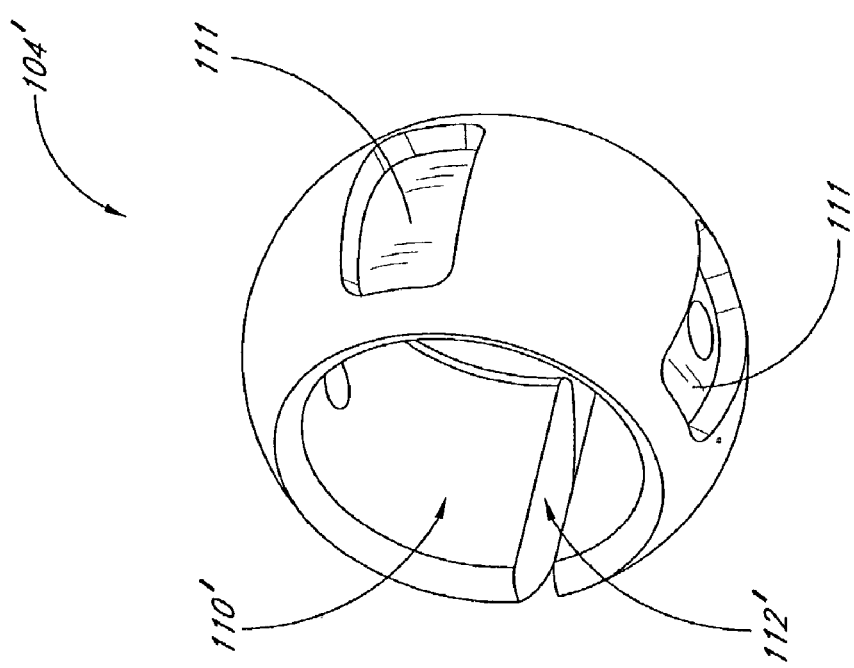
FIG. 3B illustrates an angularly adjustable connector with rotation limits according to another embodiment.

FIG. 3B illustrates an alternate connector 104'. Similar to the connector 104 described above, the connector 104' is provided with an aperture 110' having a longitudinal axis and a gap 112'. The spherical exterior surface of the connector 104' is provided with one or two or three or more surface structures such as projections or indentations 111. The indentations 111 receive complementary surface structures such as projections provided within the head 108 of the bone anchor 100 to limit the degree of rotation of the connector 104' within the head 108. For example, FIG. 3G illustrates an exemplary embodiment wherein the complementary surface structure comprises a pin 101 that may be laser welded or otherwise coupled to or integrally formed with the screw head 108. As described above, the pin 101 interacts with the indentation 111 to limit the degree of rotation of the connector 104' within the head 108. In one specific embodiment, the connector 104' is limited to about 30 degrees of rotation on any axis within the head 108, from the longitudinal axis through the transverse portal 116. In other embodiments, the connector 104' may be limited to a range of up to about 60 degrees of rotation from the longitudinal axis. In one embodiment, the connector 104' is limited to no more than about 5 degrees or about 10 degrees of rotation on any axis from the longitudinal axis.

In general, the rotation of the connector 104' is limited such that the aperture will always be exposed through transverse portal 116 to the linkage rod 200. As can be seen, for example, in FIG. 4, below, the linkage rod 200 may be provided with a tapered distal end 201. The tapered distal end 201 may be machined or molded integrally with the linkage rod 200, or may be separately formed and attached to the linkage rod 200. In one implementation, the tapered end 201 may be a polymeric component such as nylon, HDPE, PEBAX or other materials known in the art. The tapered tip 201 facilitates advance of the linkage rod 200 through aperture 110, by causing the connector 104 to pivot about its center of rotation into alignment for receiving the linkage rod 200. In this manner, the connector 104 will self align with the linkage rod 200 to accommodate any of a wide variety of angular relationships that may be found in vivo.

Figure 3C:
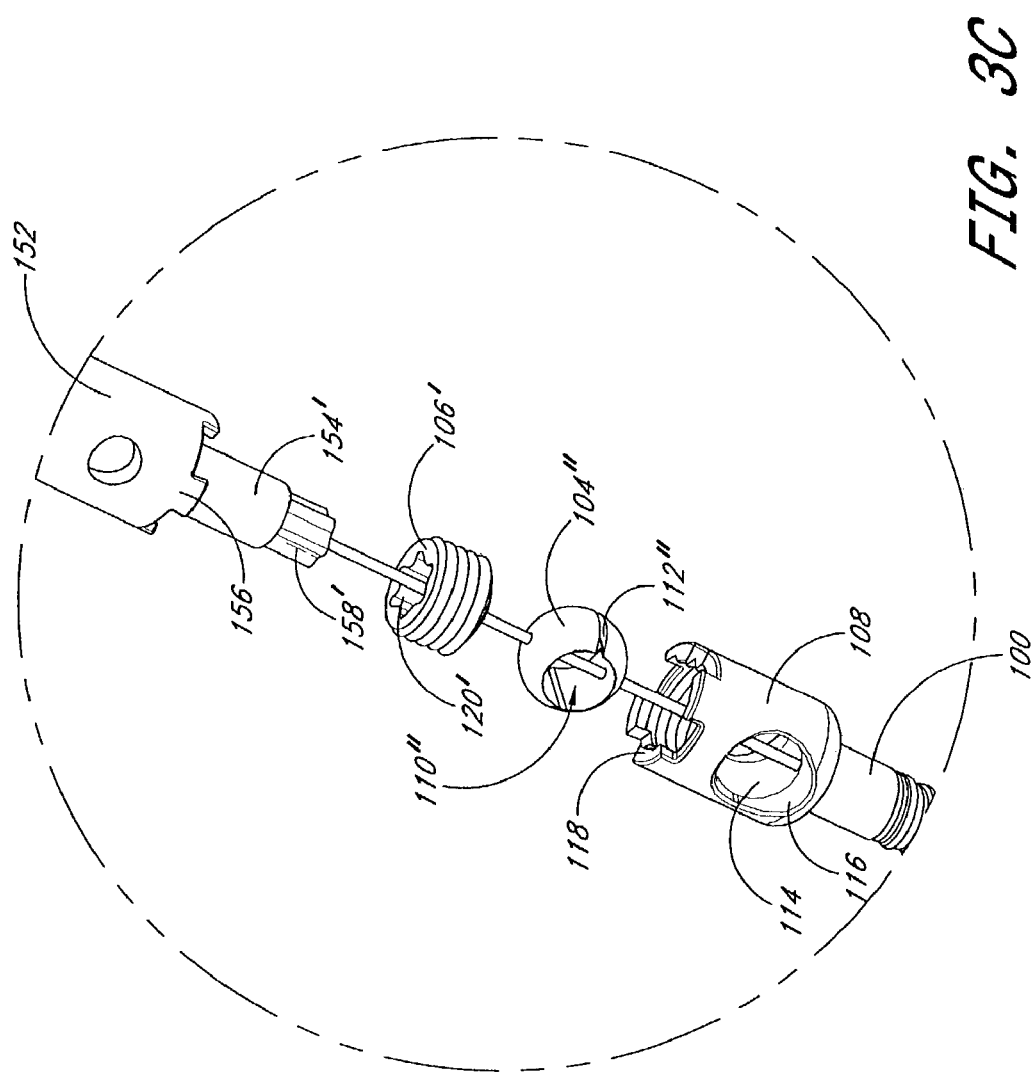
FIG. 3C illustrates a connector, a locking cap and its complementary inner adapter according to yet another embodiment.

FIG. 3C is similar to FIG. 3A above, and illustrates an inner adapter 154' and a locking cap 106' according to another embodiment. In one embodiment, the inner adapter 154' is provided with a Torx distal end 158' which is adapted to engage a complementary Torx opening 120' at the top of the locking cap 106'. Any of a variety of complementary surface structures may be used, as will be understood in the art in view of the disclosure herein.

FIG. 3C illustrates a connector 104" according to another embodiment. Similar to the connectors 104 and 104' described above, the connector 104" is provided with an aperture 110" and one or more compressible gaps 112". The gaps 112" are provided with a compressible material which compresses when the locking cap 106' tightens the connector 104" against the groove 114 within the head 108. Compressible material, including any of a variety of compressible polymeric materials known in the medical device arts can be used according to several embodiments of the present invention. One skilled in the art will appreciate that other suitable flexible or compressible materials may also be used. In addition, any of a variety of metal (stainless steel, titanium, etc.) connectors 104 may be configured such that the aperture 110 is moveable from a first, large cross-section, for receiving a linkage rod 200 therethrough, to a second, reduced cross section for locking the linkage rod 200 in place. This may be accomplished by providing opposing components forming the side wall of the connector 104 with any of a variety of interlocking structures such as ramp and pawl ratchet structures, or sliding fit structures which permit a reduction in the diameter in the aperture 110 under compressive force from the locking cap 106.

In an alternate embodiment, portions or all of the connector 104 comprise a compressible media such as an open cell foam, closed cell foam or solid compressible material. Structures comprising polyethylene, PEEK, nylon, and other polymers known in the medical arts may be utilized, depending upon the construction and desired compressibility. In general, the combination of material and the structure of the connector 104 is sufficient to allow angular adjustment of the longitudinal axis of the aperture 110, to accommodate various entrance angles of the linkage rod 200. After the linkage rod 200 has been positioned within the aperture 110, rotational and/or axial movement of a locking element such as locking cap 106 functions to both prevent axial movement of the linkage rod 200 within the aperture 110, as well as prevent further angular adjustment of the longitudinal axis of the aperture 110 with respect to the longitudinal axis of the bone anchor 100.

Figure 3E:
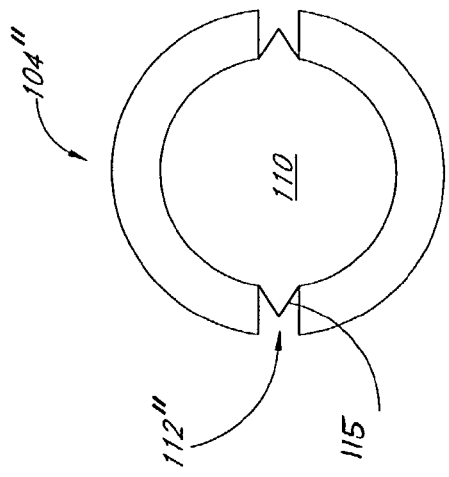
FIGS. 3D-3F illustrate the connector illustrated in FIG. 3C in further detail.
Figure 3D:
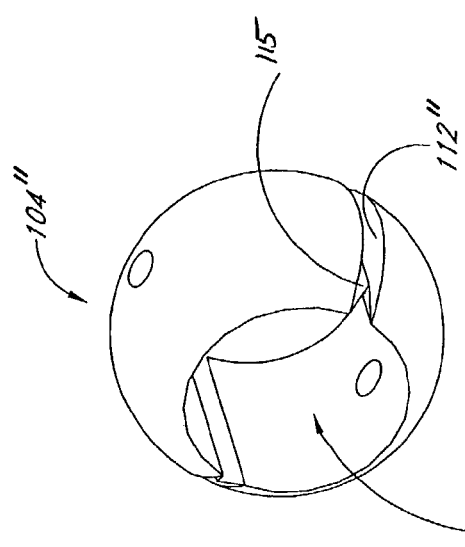
Figure 3F:
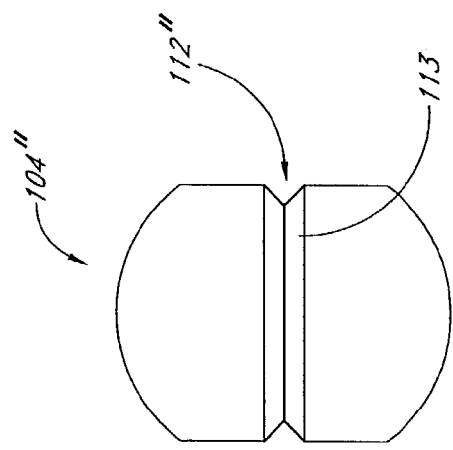
Figure 3G:
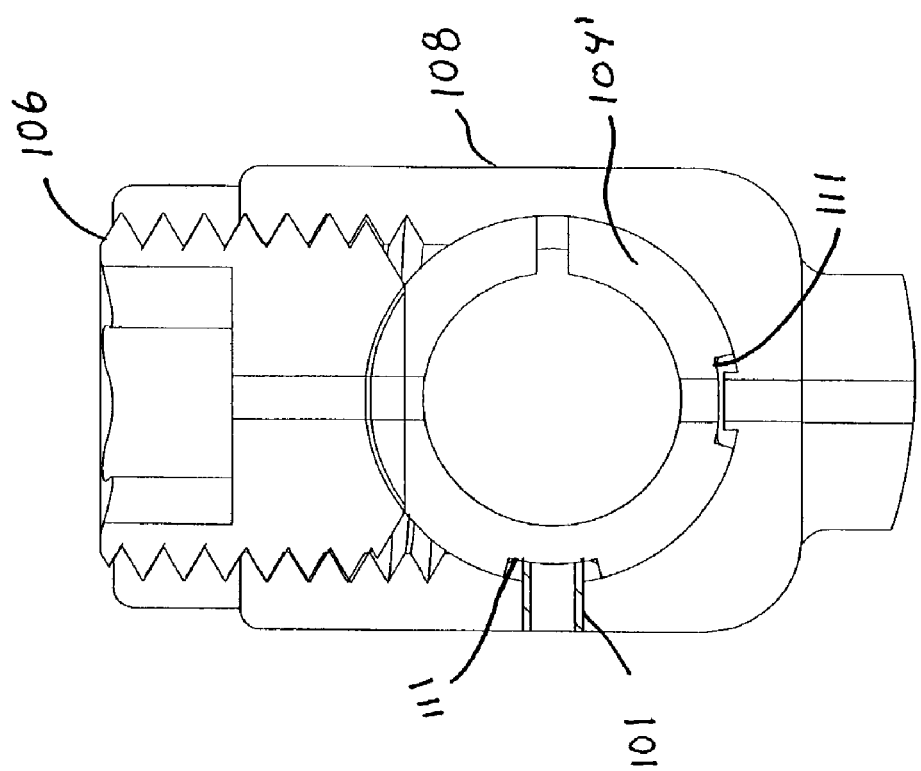
FIG. 3G is a cross-sectional view of an angularly adjustable connector with rotation limits positioned within a head of a bone anchor according to another embodiment.

FIGS. 3D-3F illustrate the connector 104", the aperture 110", the gaps 112", and a compressible or foldable membrane or link 115 in greater detail. FIG. 3D is an isometric view of the connector 104". FIG. 3E is a front plan view of the connector 104" viewed along the central axis of the aperture 110". FIG. 3F is the corresponding side plan view. In the embodiment illustrated in FIGS. 3D-3F, the compressible link is formed by grinding, laser etching, molding or otherwise forming a recess such as a V-shaped channel 113 that leaves a thin link 115 which folds flat when the connector 104" is compressed. One of ordinary skill in the art will understand that compressible materials and structures can be provided in a variety of suitable shapes and forms.

In one embodiment, the apertures 110' and 110" have a tendency to return to their original diameters even after the connectors 104 and 104', respectively, are compressed by the locking cap 106 against the groove 114 within the head 108. This tendency results from the resiliency of the metal, alloy or other material used to make the connectors 104 and 104'. The use of compressible material, such as V-shaped channels 113 in the gaps 112" of the connector 104", reduces or eliminates this tendency and may allow a linkage rod (not shown) to be more firmly secured within the aperture 110". One skilled in the art will understand that the connectors 104 and 104' can be made from lower resiliency materials which can also reduce or eliminate the tendency of apertures 110' and 110" to return to their original diameters.

As discussed above with reference to FIG. 2, in one embodiment, the outer adapter 152 is adapted to engage the head 108, and the inner adapter 154 is adapted to engage the locking cap 106. In the illustrated embodiment, projections 156 on the distal end of the outer adapter 152 are adapted to engage complementary projections 118 on the head 108 of the bone anchor 100. The hexagonal distal end 158 of the inner adapter 154 is adapted to engage a complementary hexagonal opening 120 at the top of the locking cap 106.

Although specific interlocking relationships between the driver 150 and the bone anchor 100 are illustrated herein, the present inventors contemplate a variety of modifications. For example, the male-female relationship between the driver and the implant may be reversed, for either or both of the inner adaptor 154 and outer adapter 152. In addition, each of the inner adapter 154 and outer adapter 152 is provided with a surface structure for enabling rotational engagement with a corresponding component on the implant. Although this may be conveniently executed using corresponding hexagonal male and female components, any of a variety of alternative structures may be utilized in which a first surface on the inner adapter 154 or outer adapter 152 cooperates with a second, complementary surface on the corresponding aspect of the bone anchor 100, for allowing rotational engagement, followed by axial decoupling.

Figure 4:
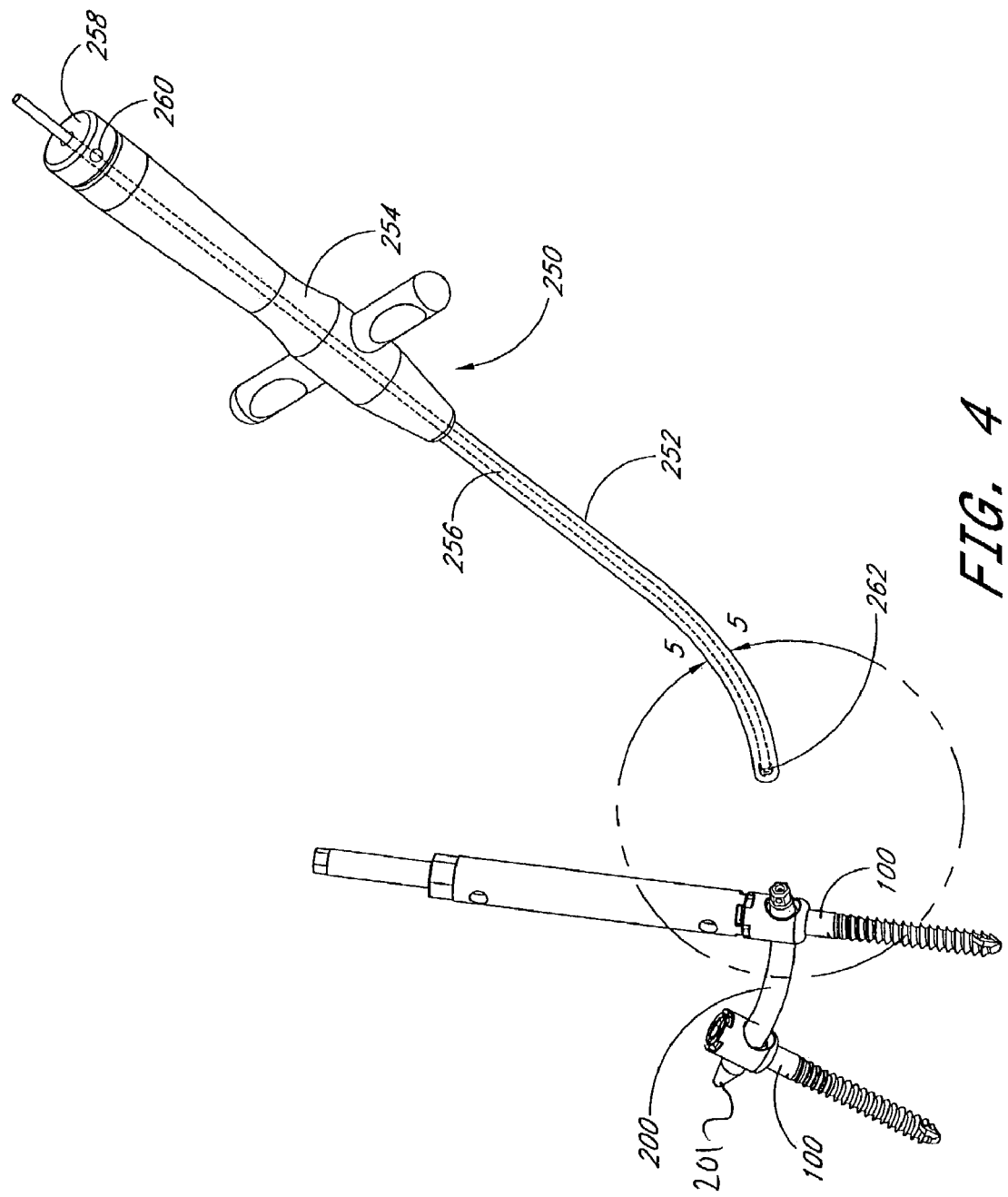
FIG. 4 is another view of the system for minimally invasive posterior spinal fixation illustrated in FIG. 1, with the linkage rod detached from its insertion tool.

In FIG. 4, the linkage rod 200 is shown positioned within two adjacent bone anchors 100, and released from the insertion tool 250. The insertion tool 250 is provided for the insertion of the linkage rod 200 into the bone anchors 100. The insertion tool 250 comprises an arm 252 and a handle 254. In the illustrated embodiment, the arm 252 is curved to facilitate insertion of the linkage rod 200 into the bone anchors 100 within a patient along a curved tissue tract which passes through the aperture 110 of at least each of a first bone anchor and a second bone anchor. A central control line 256 (shown mostly in phantom) such as a torque transmission tube, rod or cable extends through an axial lumen of the insertion tool 250, and terminates at a control such as a knob 258 at the proximal end of the insertion tool 250. A screw (not shown) threaded into a tunnel 260 extending along a radius of the knob 258 may be used to secure the control line 256 within the knob 258. The control line 256 is provided with a threaded distal tip 262. Rotating the knob 258 thus rotates the control line 256 and its threaded distal tip 262 to engage or disengage the linkage rod 200.

In one embodiment, both the linkage rod 200 and the control line 256 are provided with a central axial lumen for the passage over a guide wire.

Figure 5:
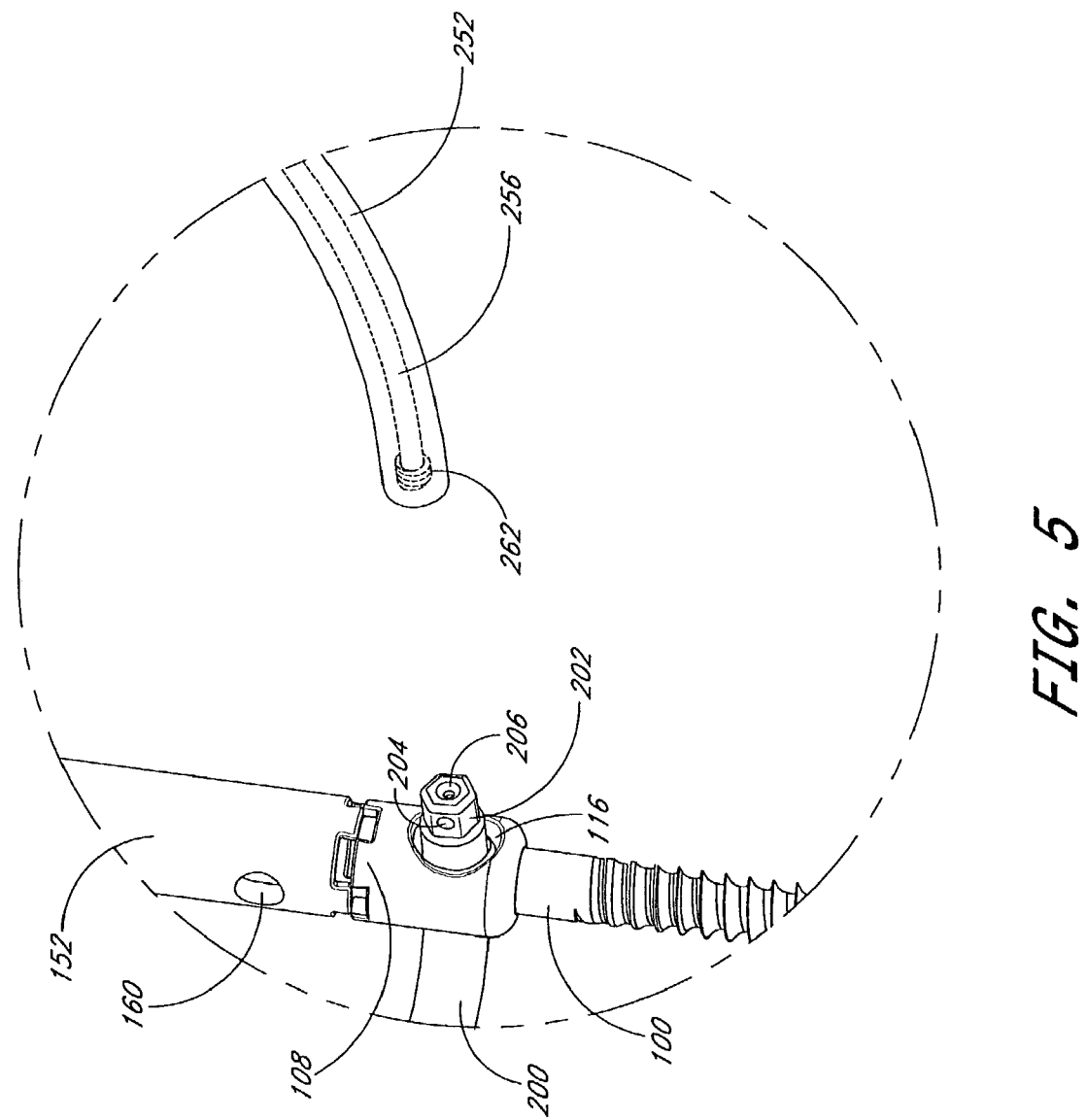
FIG. 5 is an enlarged view of the circled area in FIG. 4.

FIG. 5 is an enlarged view of the circled area in FIG. 4, showing the distal end of the outer adapter 152, the bone anchor 100, the linkage rod 200, and the distal end of the arm 252 of the insertion tool. The linkage rod 200 is shown fixed within the head 108 of the bone anchor 100.

The linkage rod 200 is provided with a hexagonal proximal end 202 adapted to engage a complementary hexagonal socket (not shown) in the distal end of the arm 252 of the insertion tool. In some embodiments, alternative complementary surface structures may be provided on the linkage rod 200 and the arm 252 to rotationally fix their orientation with respect to one another. In the illustrated embodiment, the hexagonal proximal end 202 is provided with a dimple 204 adapted to engage a complementary nub (not shown) within the hexagonal socket (not shown) in the distal end of the arm 252 of the insertion tool. The dimple 204 and nub (not shown) fix the axial orientation of the linkage rod 200 with respect to the arm 252. The threaded distal tip 262 of the control line 256 may be threaded into a complementary threaded hole 206 in the hexagonal proximal end 202 of the linkage rod 200, enabling the linkage rod 200 to be detachably secured to the arm 252 of the insertion tool. The threaded distal tip 262 may be threaded into the threaded hole 206 by rotating the knob (not shown) at the proximal end of the insertion tool. Unthreading the threaded distal tip 262 from the threaded hole 206 allows the linkage rod 200 to be released from the insertion tool 250.

In one embodiment, the outer adapter 152 is provided with an opening 160 extending along a diameter for fluoroscopic or other visualization of the rotational orientation of the outer adapter 152, to align the portal 116 of the bone anchor 100 engaged by the outer adapter 152. Towards this end, the axis of the opening 160 is preferably arranged at a right angle to the axis of the portal 116 as shown in FIG. 5. To visualize the axial position of the outer adapter 152 and the bone anchor 100, the inner adapter 154 may be temporarily retracted so that it does not block the opening 160. In another embodiment a translucent marker may be installed in opening 160 for fluoroscopic or other visualization of the outer adapter 152.

Alternatively, any of a variety of other indicium of the rotational orientation of the bone anchor 100 may be provided. For example, the complementary surface structures between the proximal end of the bone anchor 100 and the distal end of the insertion tool 250 may be configured to only allow coupling between the two components in a predetermined rotational orientation. In this construction, visual indicia may be provided on a portion of the insertion tool 250 (e.g. "T" handle, painted or etched markings or other indicium) which remains external to the patient, to allow direct visual observation of the rotational orientation of the longitudinal axis of the transverse portal 116.

Figure 6:
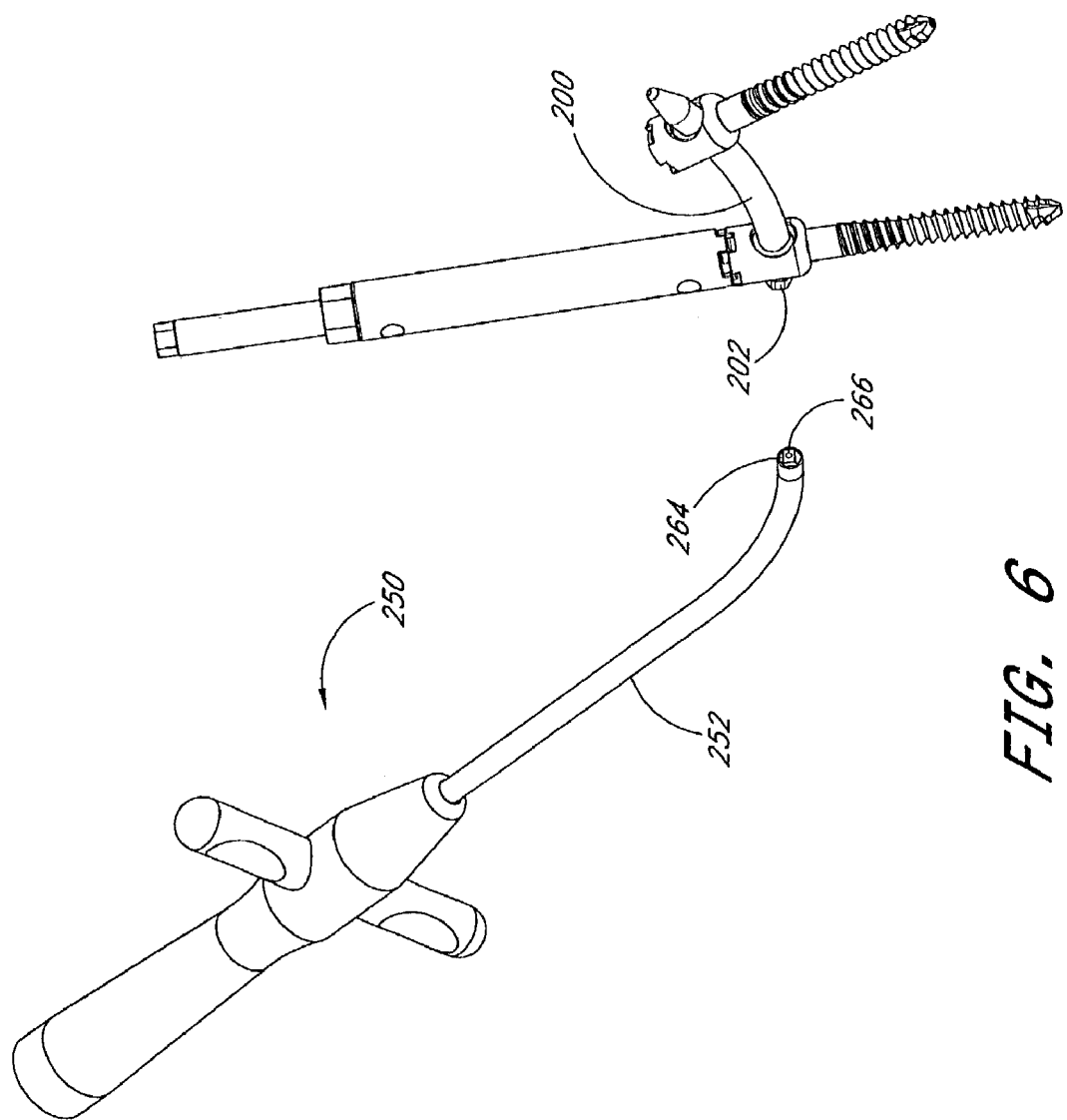
FIG. 6 is another view of the system for minimally invasive posterior spinal fixation illustrated in FIG. 4.

FIG. 6 illustrates the described system from another angle. The knob and its attached central cable have been removed for clarity. The hexagonal socket 264 adapted to engage the hexagonal proximal end 202 of the linkage rod 200, as described above, is shown. The nub 266 adapted to engage the dimple (not shown) on the hexagonal proximal end 202 of the linkage rod 200 is also shown.

In several embodiments, the components of the bone anchor, the linkage rod, the driver, and the arm of the insertion tool may be made of titanium, stainless steel or any other suitable metals, alloys, or material. The handle of the insertion tool is preferably made of a suitable non-slip material. The selection of these materials for the manufacture of the components and devices described in the above embodiments would be known by those skilled in the art.

Methods for the minimally invasive implantation of posterior fixation hardware according to embodiments of the present invention are disclosed in the context of a spinal fixation procedure with reference to FIGS. 7-45. Additional details concerning the method are disclosed in the copending patent applications incorporated by reference previously herein. Although the methods and instruments of the present invention can be utilized in an open surgical procedure, the present invention is optimized in the context of a percutaneous or minimally invasive approach. Thus, the method steps which follow and those disclosed in the copending patent applications incorporated by reference herein are intended for use in a trans tissue approach. However, to simplify the illustrations, the soft tissue adjacent the treatment site is not illustrated in the drawings discussed below.

Figure 7:
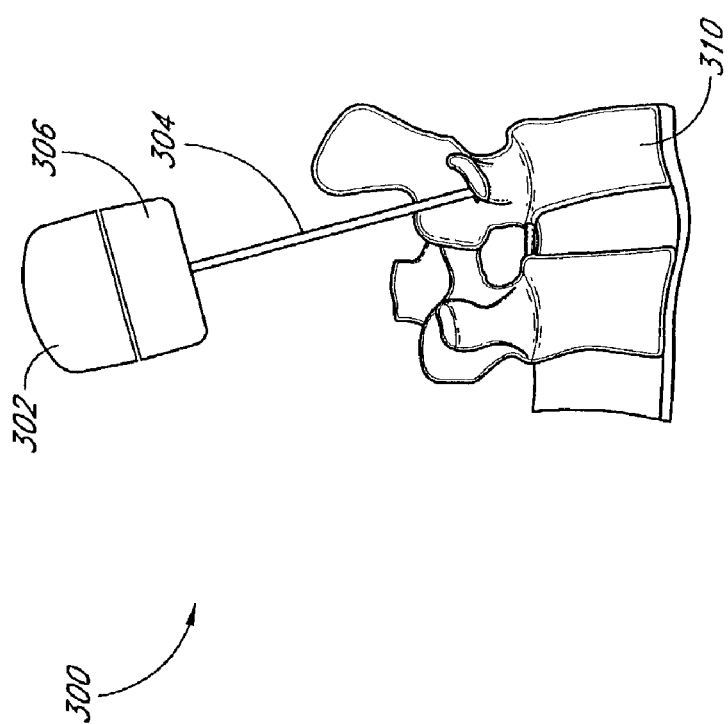
FIGS. 7-12 illustrate the use of positioning tools to position a guide wire into a vertebral body.
Figure 8:
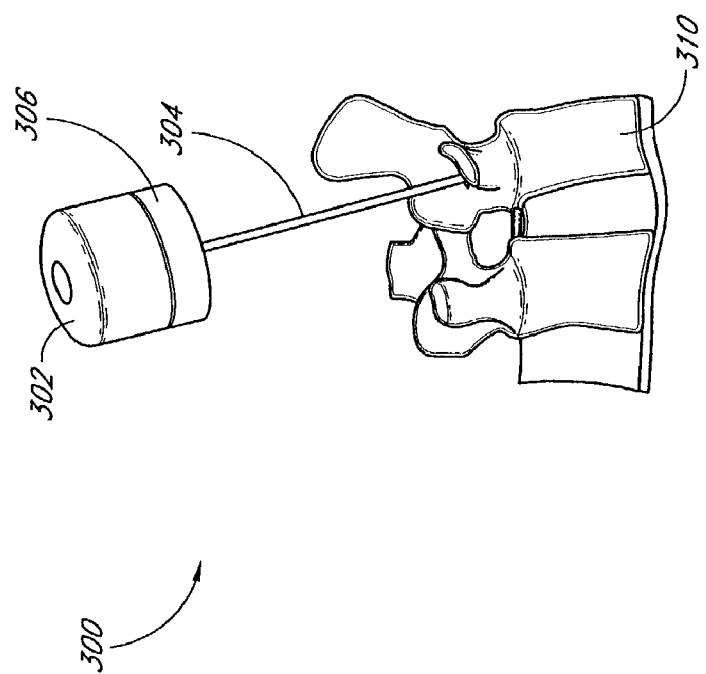

In FIGS. 7 and 8, a trocar 300 is inserted through a tissue tract and into a vertebral body 310. The trocar 300 comprises a sharp-tipped rod (not shown) attached to a proximal or top half-handle 302. The sharp-tipped rod is arranged concentrically within a cannula 304, which is attached to the bottom half-handle 306 of the trocar 300. The top half-handle 302 and the bottom half-handle 306 of the trocar 300 are screwed together for initial use, as shown in FIGS. 7-8. The trocar 300 is inserted through the skin, muscle and other tissues of the patient into the vertebral body 310.

Figure 16:
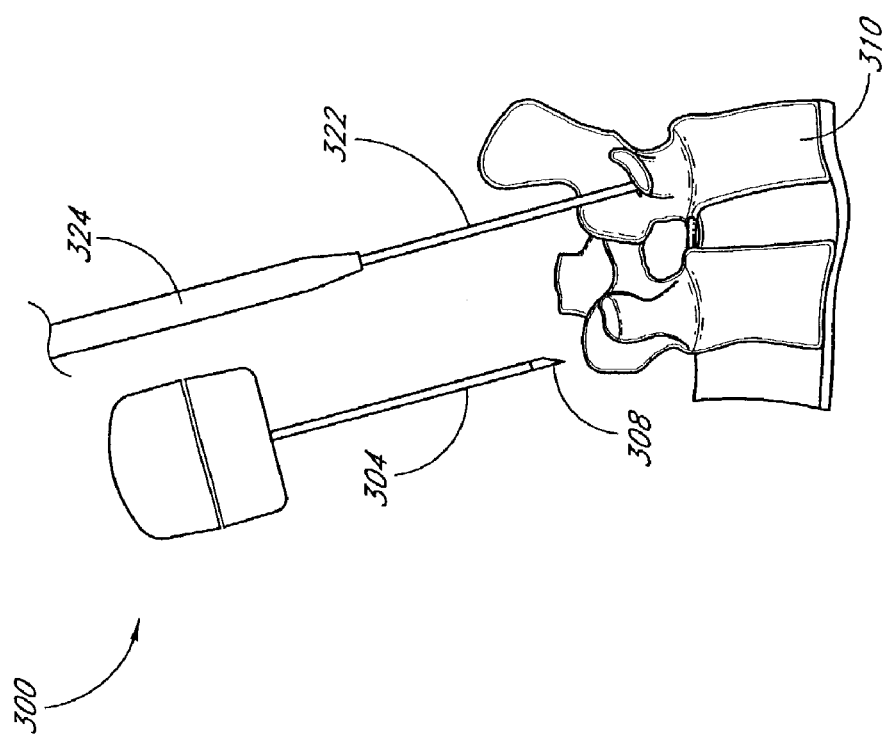

The tip 308 of the sharp-tipped rod is visible in FIG. 16.

Figure 9:
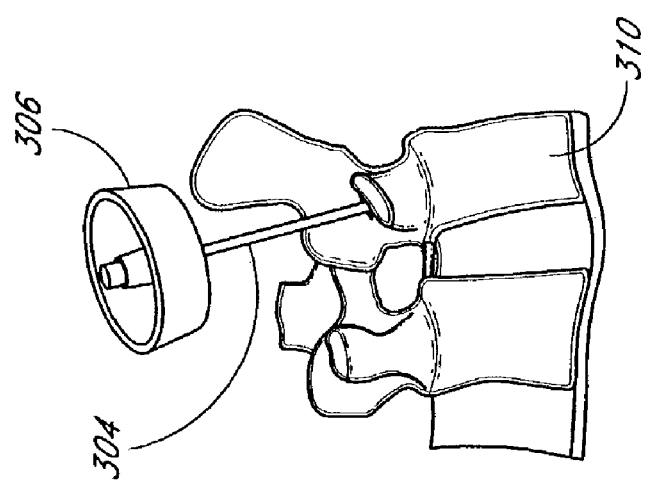
Figure 10:
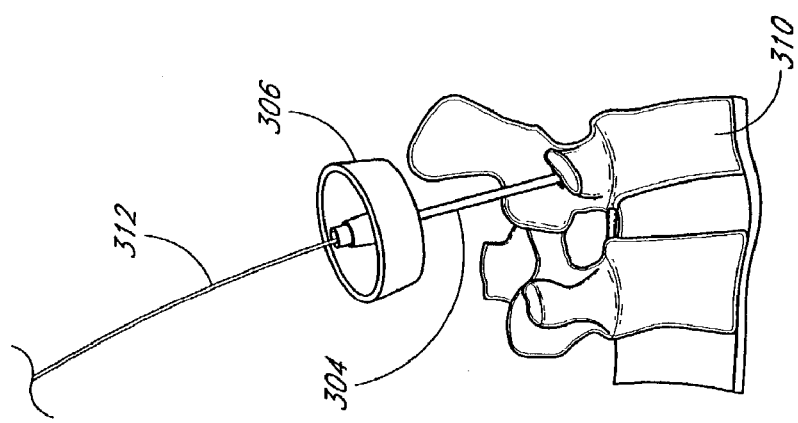

FIG. 9 shows the bottom half-handle 306 with the attached cannula 304 embedded in the vertebral body 310. The top half-handle (not shown) has been unscrewed and set aside from the bottom half-handle 306. In FIG. 10, a guide wire 312 is inserted into the vertebral body 310 via the bottom half-handle 306 and the cannula 304.

Figure 11:
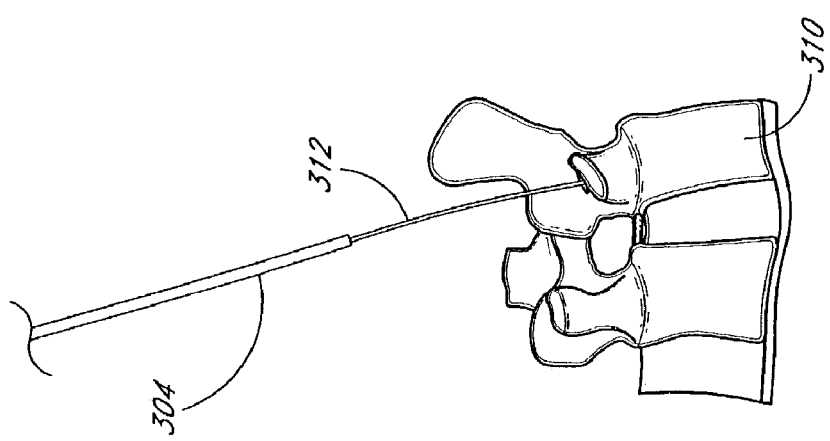

In FIG. 11, the bottom half-handle 306 and the cannula 304 are removed from the vertebral body 310. Preferably, the guide wire 312 remains in place in the vertebral body 310.

Figure 12:
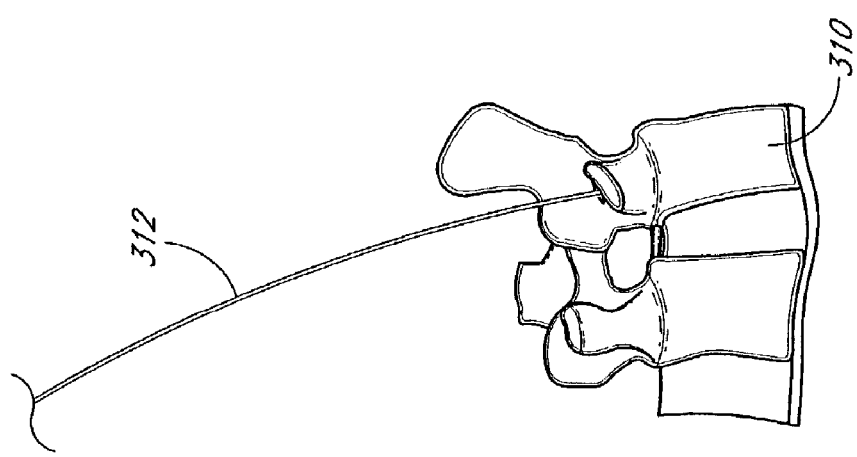

FIG. 12 shows the guide wire 312 in the vertebral body 310 after the bottom half-handle 306 and the cannula 304 are removed.

Figure 13:
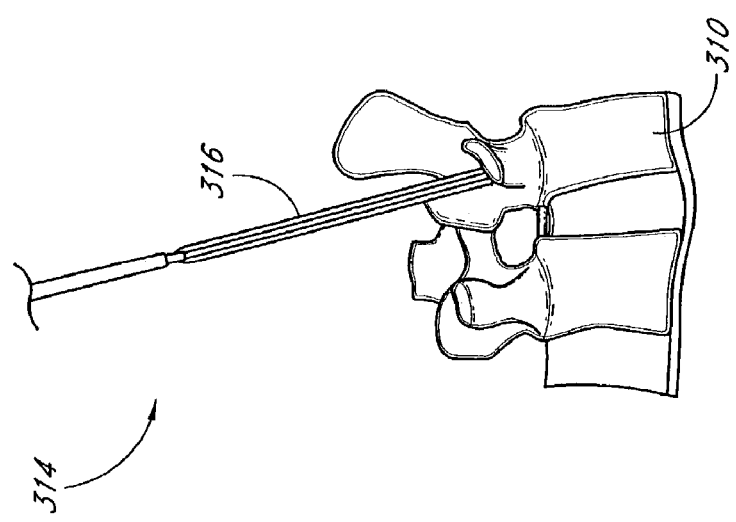
FIGS. 13-14 illustrate the use of a dilation balloon catheter to dilate a tissue tract.
Figure 14:
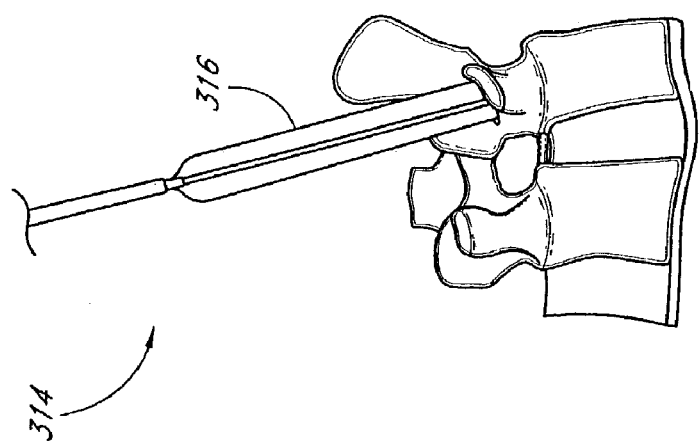

FIGS. 13-14 show one embodiment of the invention in which an inflatable tissue expander for enlarging the tissue tract is used. In FIG. 13, a balloon catheter 314 carrying a balloon 316 is advanced over the guide wire 312 towards the vertebral body 310. In FIG. 14, the balloon 316 is inflated to dilate the tissues adjacent the access pathway to the vertebral body 310. This provides an enlarged path for the insertion of a sheath as described below.

Figure 15:
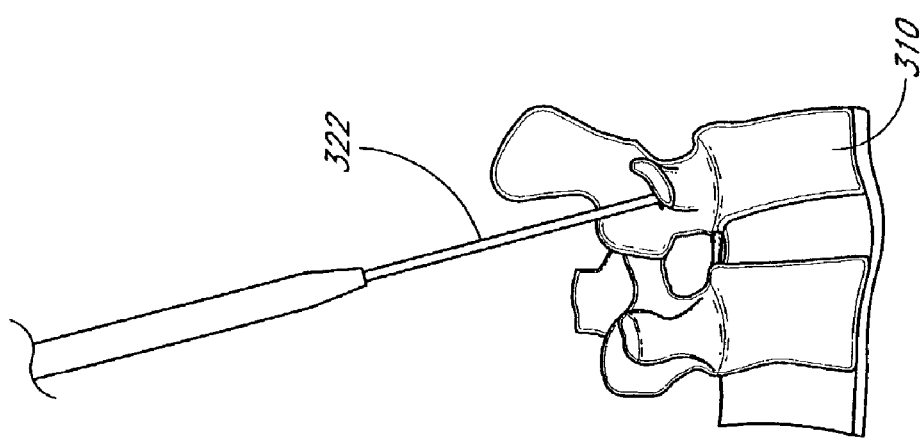
FIGS. 15-20 illustrate the positioning of a sheath adjacent to a vertebral body.

In FIG. 15, a guide tube 322 is advanced over the guide wire 312 into the vertebral body 310. As shown in FIG. 16, in one embodiment, the guide tube 322 may be approximately the same diameter as the cannula 304 of the trocar 300, allowing the guide tube 322 to be inserted into the opening in the vertebral body 310 created earlier by the trocar 300. The guide tube 322 acts as a stable rail over which a tapered dilation cylinder 324 may be advanced against the vertebral body 310.

Figure 17:
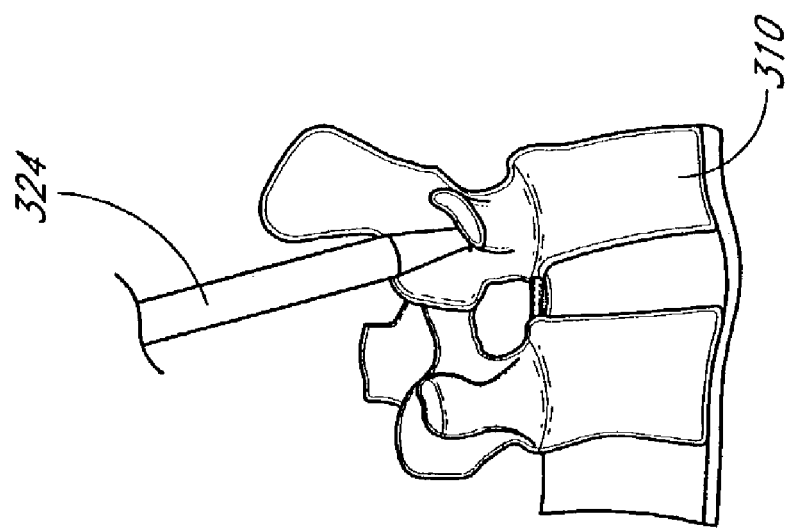

In FIGS. 16-17, a tapered dilation cylinder 324 is advanced over the guide tube 322 against the vertebral body 310. In one embodiment, the tapered dilation cylinder 324 may be approximately the same diameter as the inflated dilation balloon 316 discussed above with reference to FIGS. 13-14. The tapered dilation cylinder 324 is used to occupy the path created by the dilation balloon, and facilitates the insertion of a sheath. In an alternate sequence, the dilation cylinder 324 is provided without a tapered distal end, and is distally advanced into position directly over the inflatable balloon.

Figure 18:
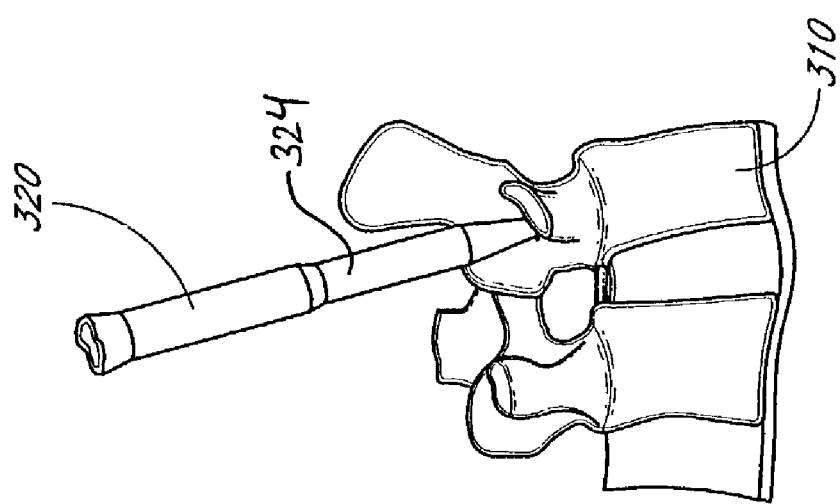
Figure 19:
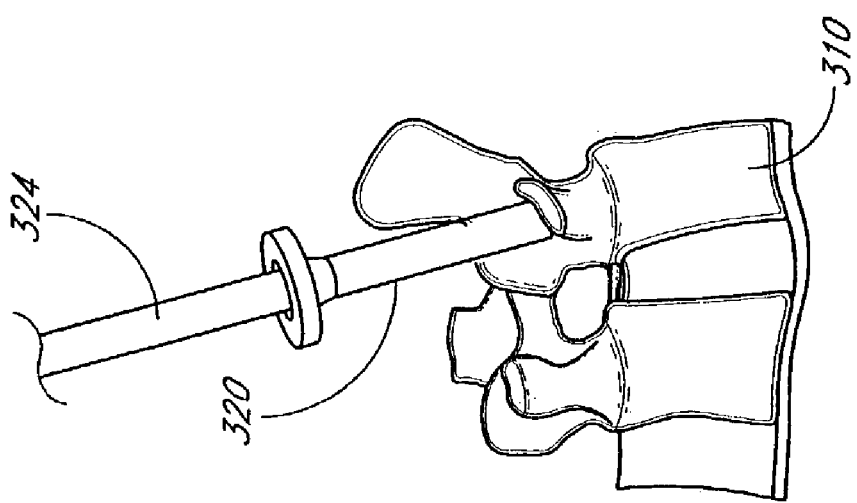
Figure 20:
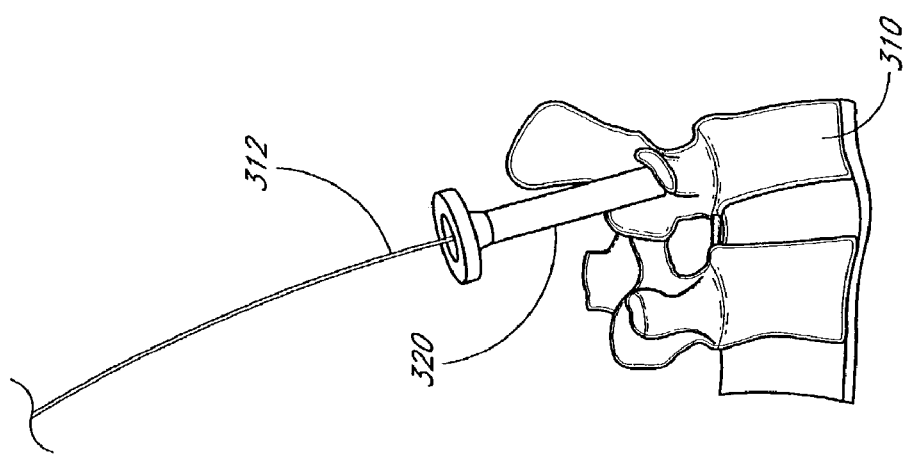

In FIGS. 18-20, a sheath 320 is advanced over the tapered dilation cylinder 324 against the vertebral body 310. The sheath 320 occupies the path created by the dilation balloon. Afterwards, the guide tube 322 and the tapered dilation cylinder 324 are removed. As shown in FIG. 20, the guide wire 312 preferably remains in the vertebral body 310 after the placement of the sheath 320.

Figure 21:
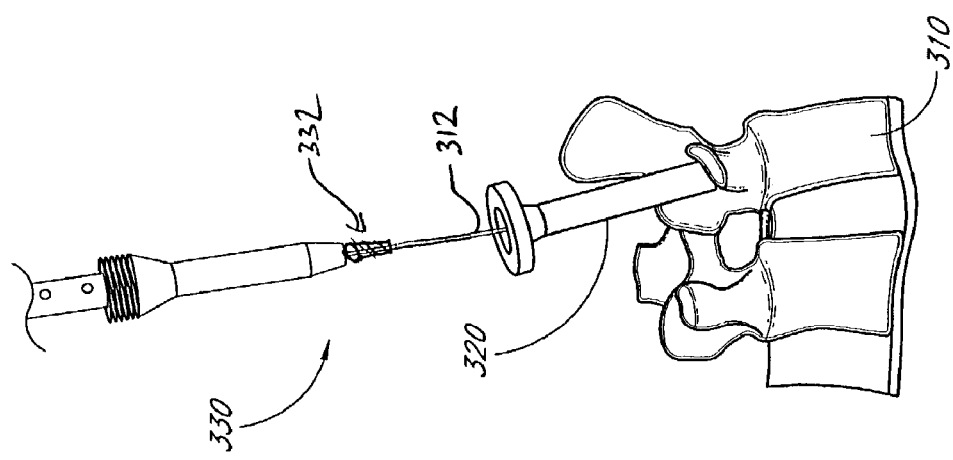
FIGS. 21-23 illustrate a drill used to create an opening in a vertebral body to receive a bone anchor.
Figure 22:
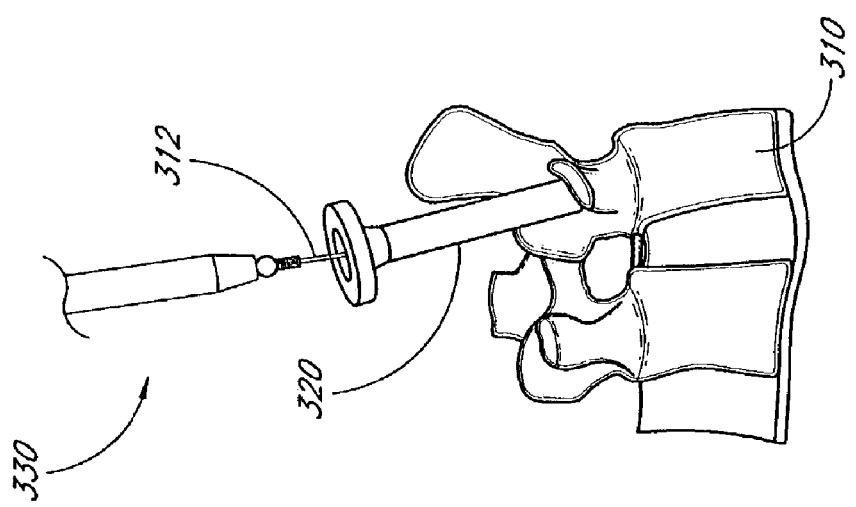
Figure 23:
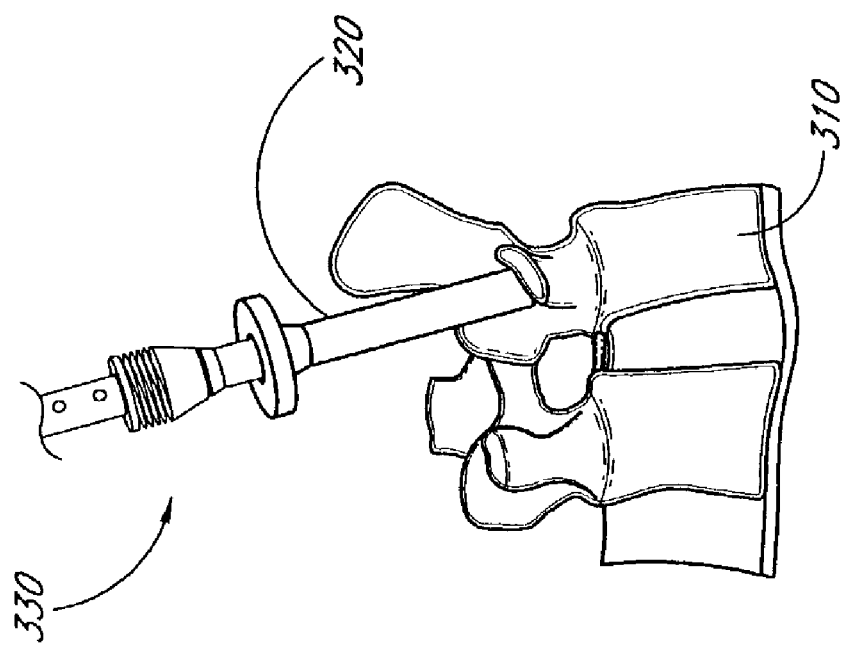

In FIGS. 21-23, a drill 330 having a rotatable distal tip 332 is advanced over the guide wire 312 and through the sheath 320. The drill 330 drills an opening (not shown) in the vertebral body 310 adapted for the insertion of a bone anchor 100.

Figure 24:
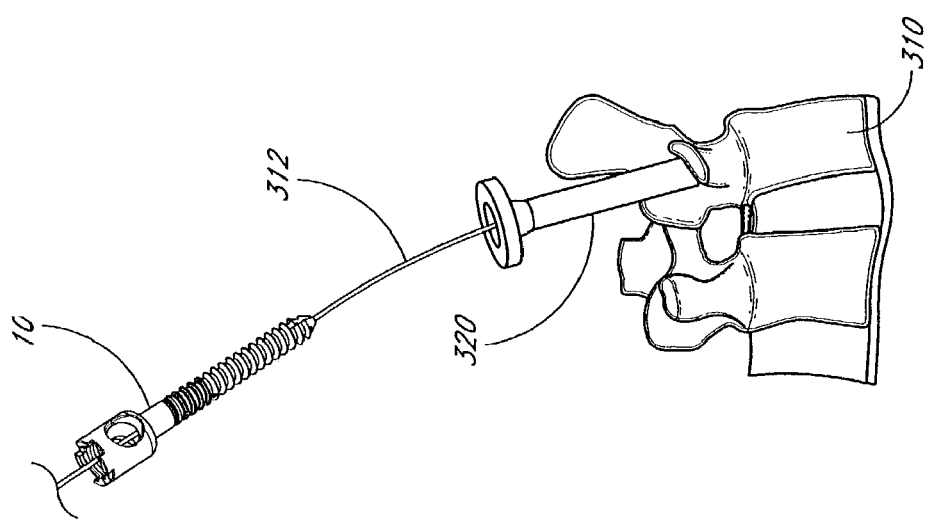
FIGS. 24-25 illustrate advancing a bone anchor over the wire towards a vertebral body.
Figure 25:
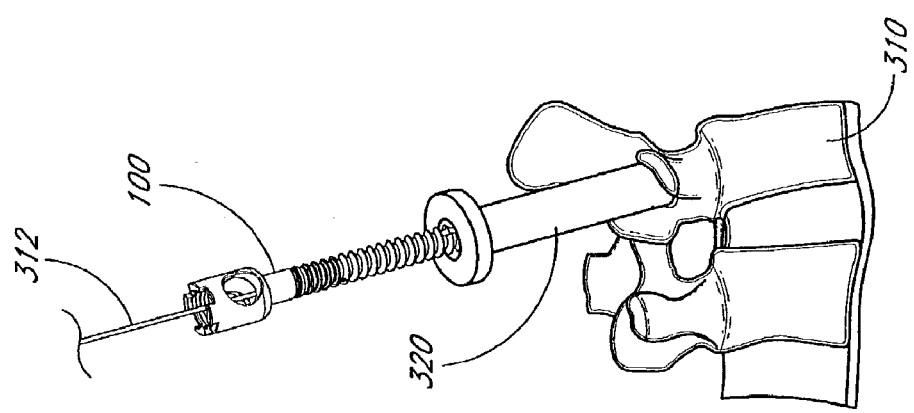

Afterwards, the drill 330 is removed. In FIGS. 24-25, the bone anchor 100 is advanced over the guide wire 312 and through the sheath 320 towards the vertebral body 310.

In FIGS. 24 and 25, a bone anchor 100 is advanced over the wire 312 and through the sheath 320 into engagement with the vertebral body 310. Although the insertion tool 250 is not illustrated, the bone anchor 100 may be coupled to the insertion tool 250 prior to the step of advancing the bone anchor 100 into contact with the vertebral body 310.

Figure 26:
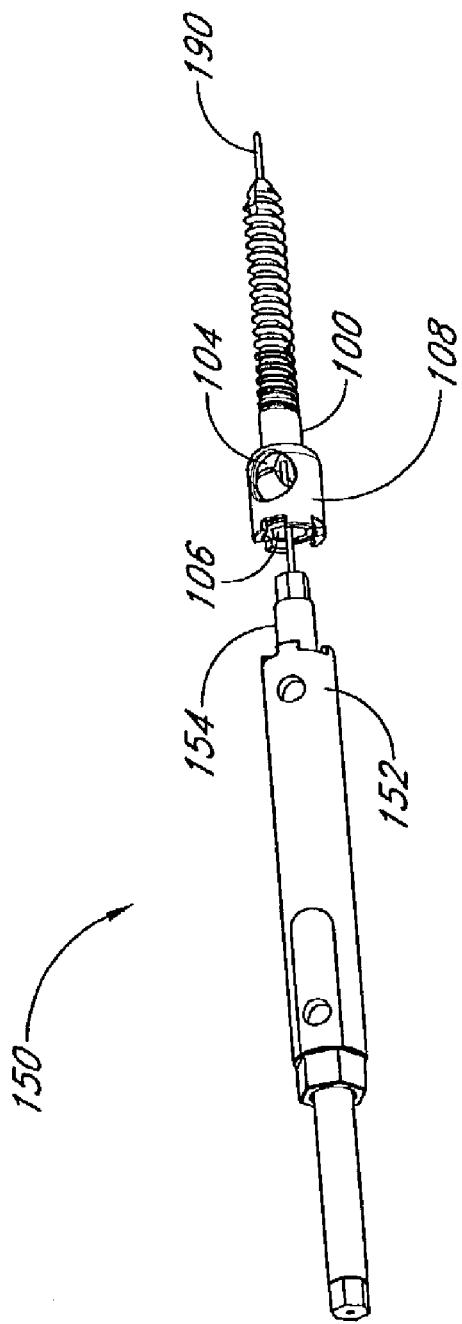
FIGS. 26-27 illustrate a bone anchor and the driver used to insert the bone anchor into a vertebral body.
Figure 27:
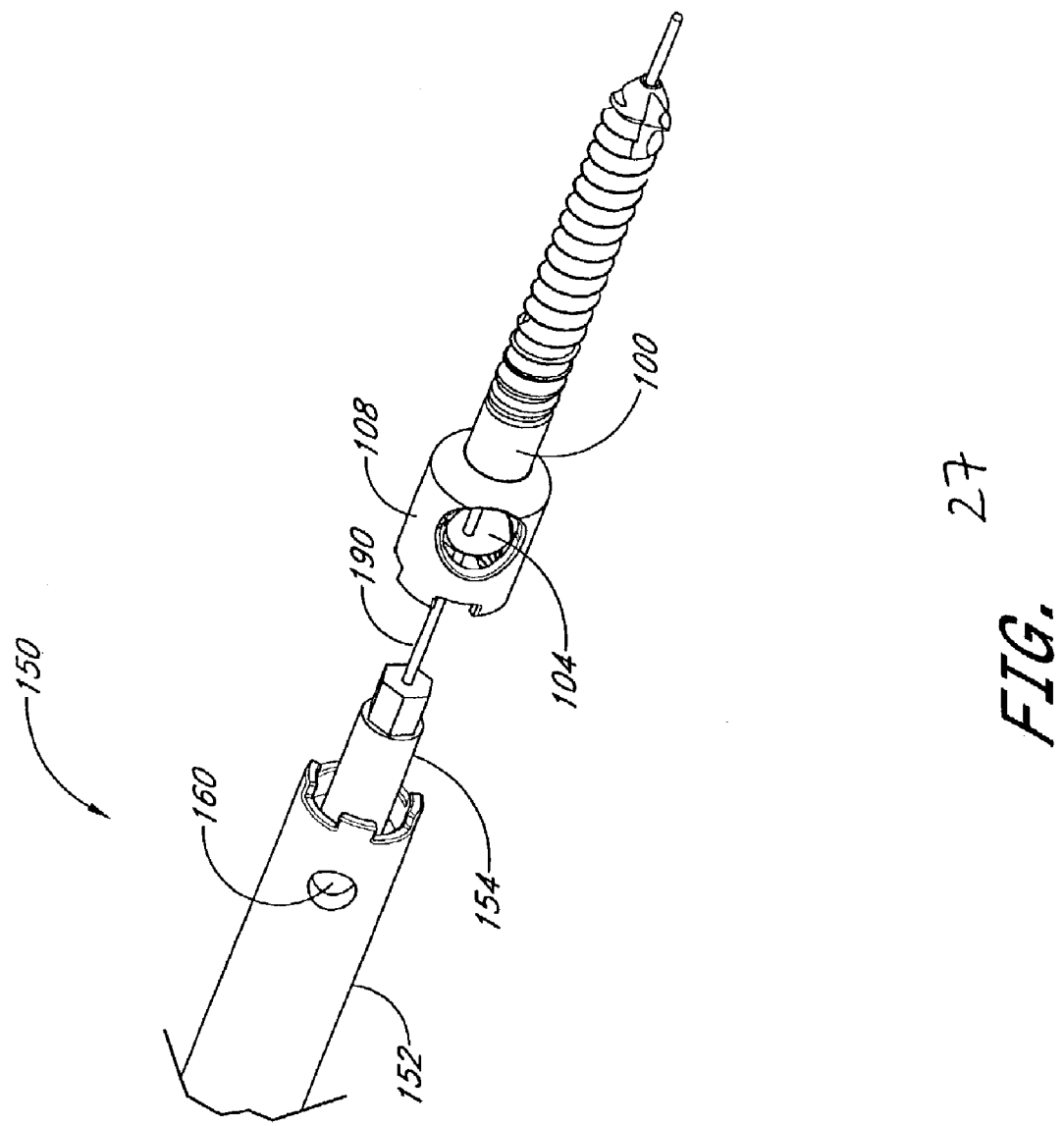
Figure 28:
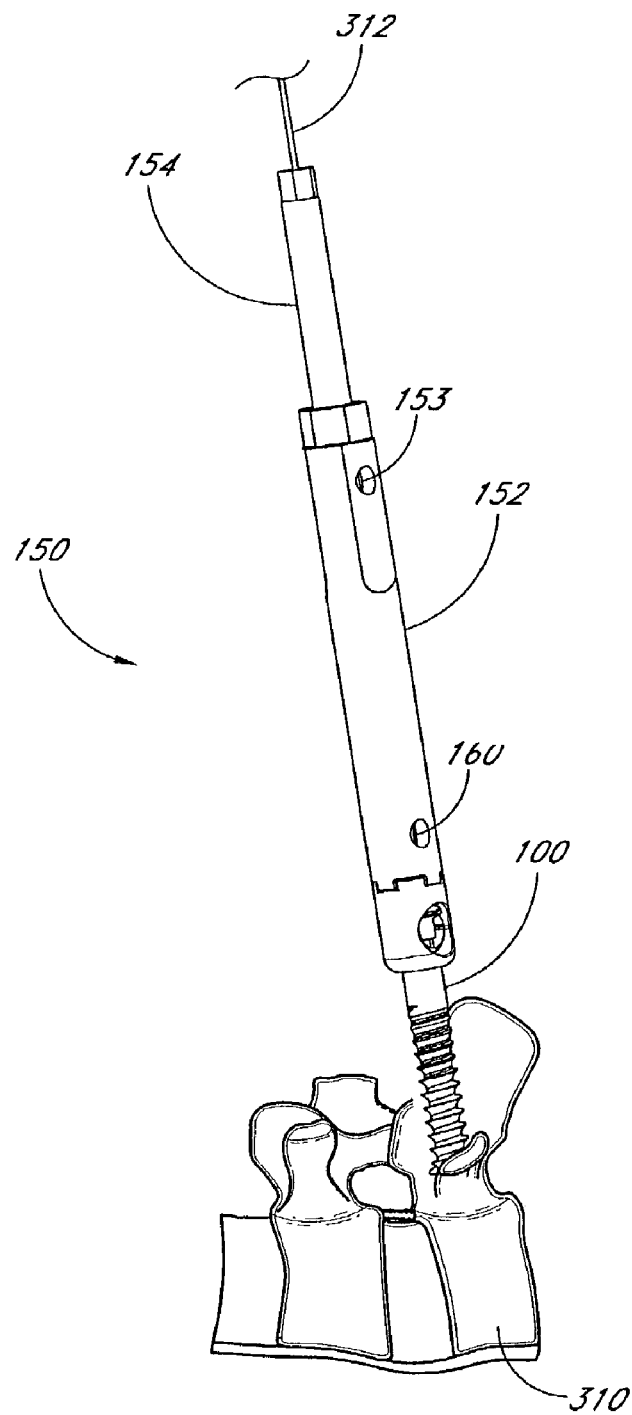
FIGS. 28-31 illustrate the use of the driver to insert a bone anchor into a vertebral body.

FIGS. 26 and 27 show the outer adapter 152 and the inner adapter 154 of the driver 150, as well as a bone anchor 100, with the connector 104 and the locking cap 106 disposed within the head 108 of the bone anchor 100. The interrelation of these components have been described in detail above with reference to FIGS. 2 and 3A. The outer adapter 152 illustrated in FIGS. 26-28 additionally comprises a pivot hole 153 which extend through a diameter of the outer adapter 152. The pivot hole 153 is adapted for the attachment of a guide wire insertion device 400 described in further detail below. In FIG. 28, these components are shown arranged over a guide wire 190.

Figure 29:
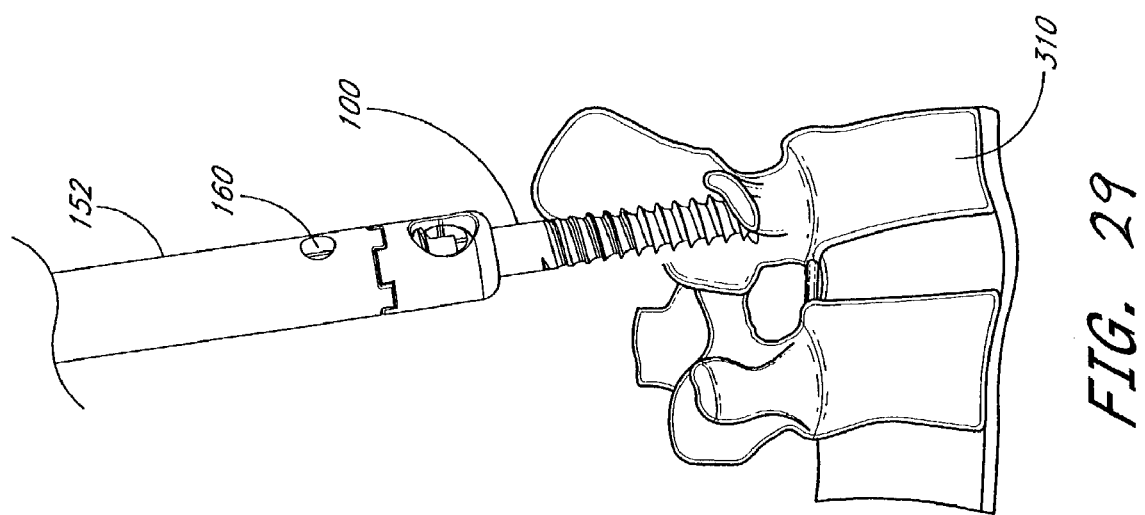
Figure 30:
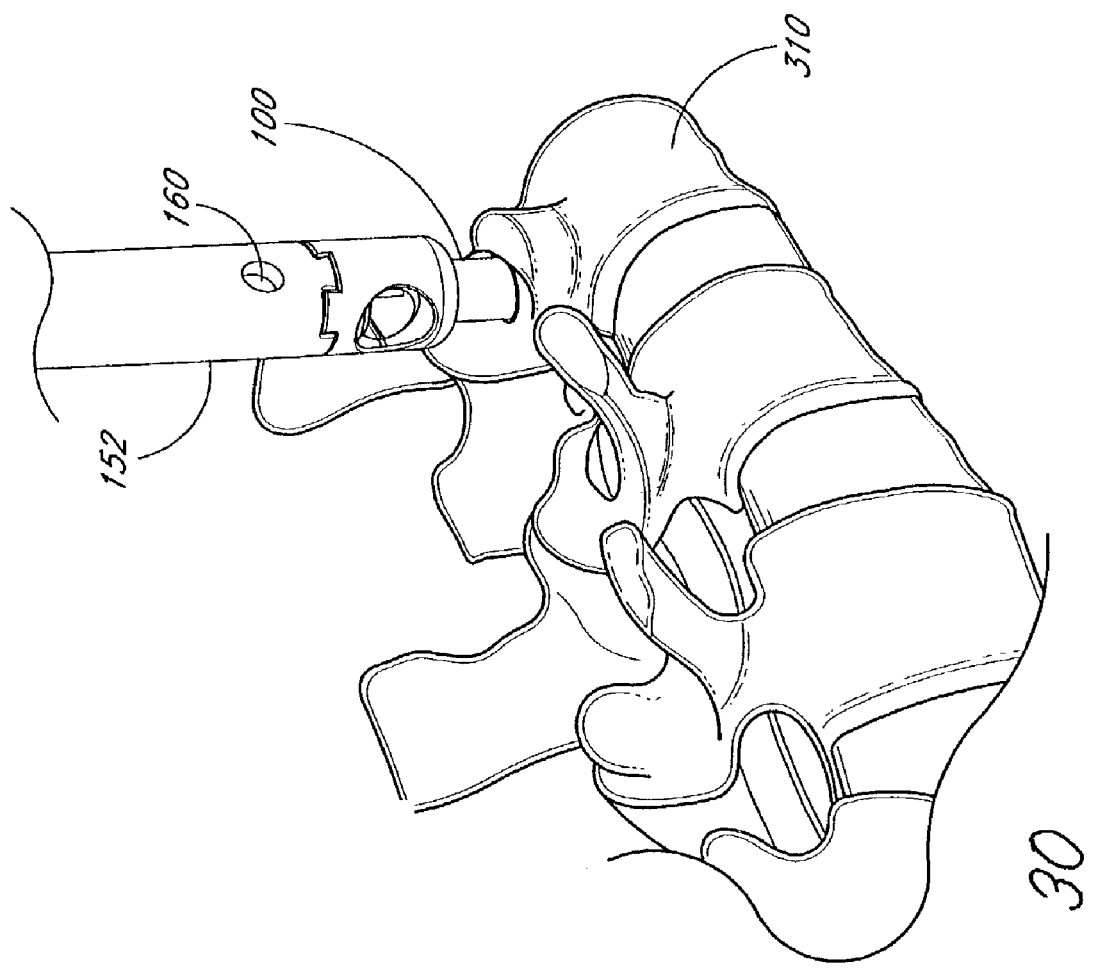
Figure 31:
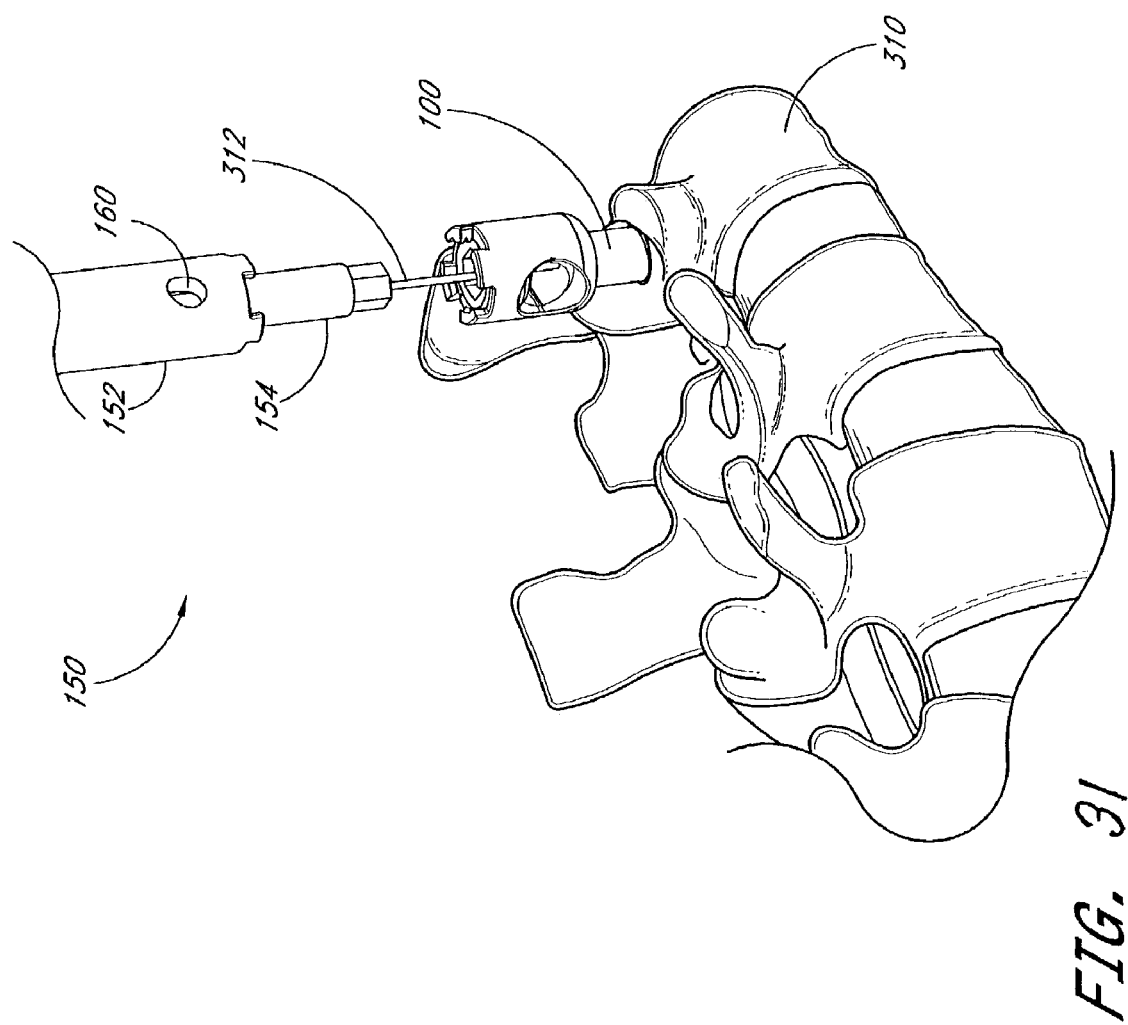

In FIG. 28, the driver 150 (comprising the outer adapter 152 and the inner adapter 154) is advanced over the guide wire 312 until the driver 150 engages the bone anchor 100. In FIGS. 29 and 30, torque is applied to the outer adapter 152 to screw the bone anchor 100 into the vertebral body 310. In FIG. 31, the driver 150 is removed, leaving the bone anchor 100 in place, with the longitudinal axis of the portal 116 aligned approximately parallel with the longitudinal axis of the spine. The sheath 320, discussed above with reference to FIGS. 18-25, while not shown in the steps discussed with reference to FIGS. 28-31, may nonetheless be used to shield the driver from adjacent tissue in these steps, as will be understood by those skilled in the art.

Figure 32:
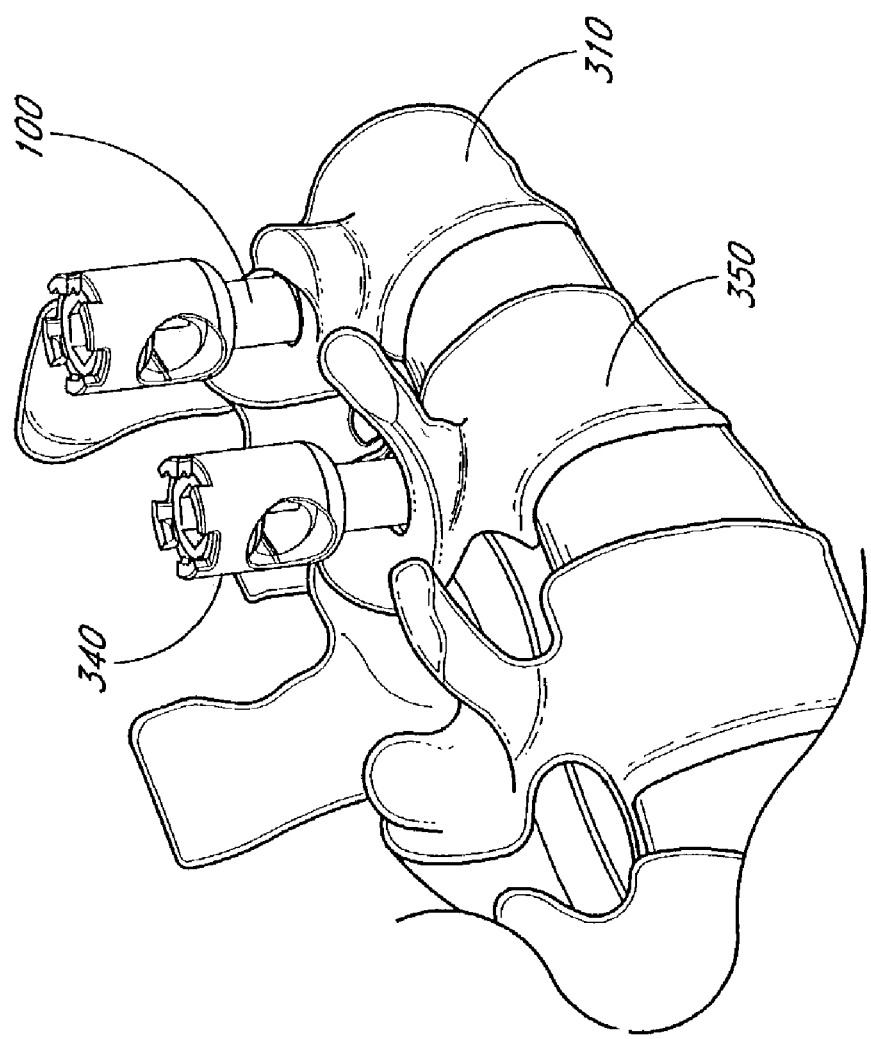
FIG. 32 illustrates two bone anchors positioned in two adjacent vertebral bodies.

In FIG. 32, a second bone anchor 340 has been inserted into another vertebral body 350. While bone anchors 100 and 340 are shown inserted into adjacent vertebral bodies 310 and 350, respectively, the system and methods for minimally invasive spinal fixation according to the embodiments of the present invention are also applicable to nonadjacent vertebral bodies. For example, a first bone anchor may be positioned in a first vertebral body as has been described above. A second bone anchor may be positioned in a second vertebral body, spaced apart from the first vertebral body by one or more intervening third vertebral bodies. The first and second bone anchors may thereafter be connected by the implantation of a linkage rod 200. Alternatively, a third bone anchor may be positioned in a third vertebral body, positioned in between the first and second vertebral bodies to produce, for example, a three level fusion system as will be discussed.

Figure 33:
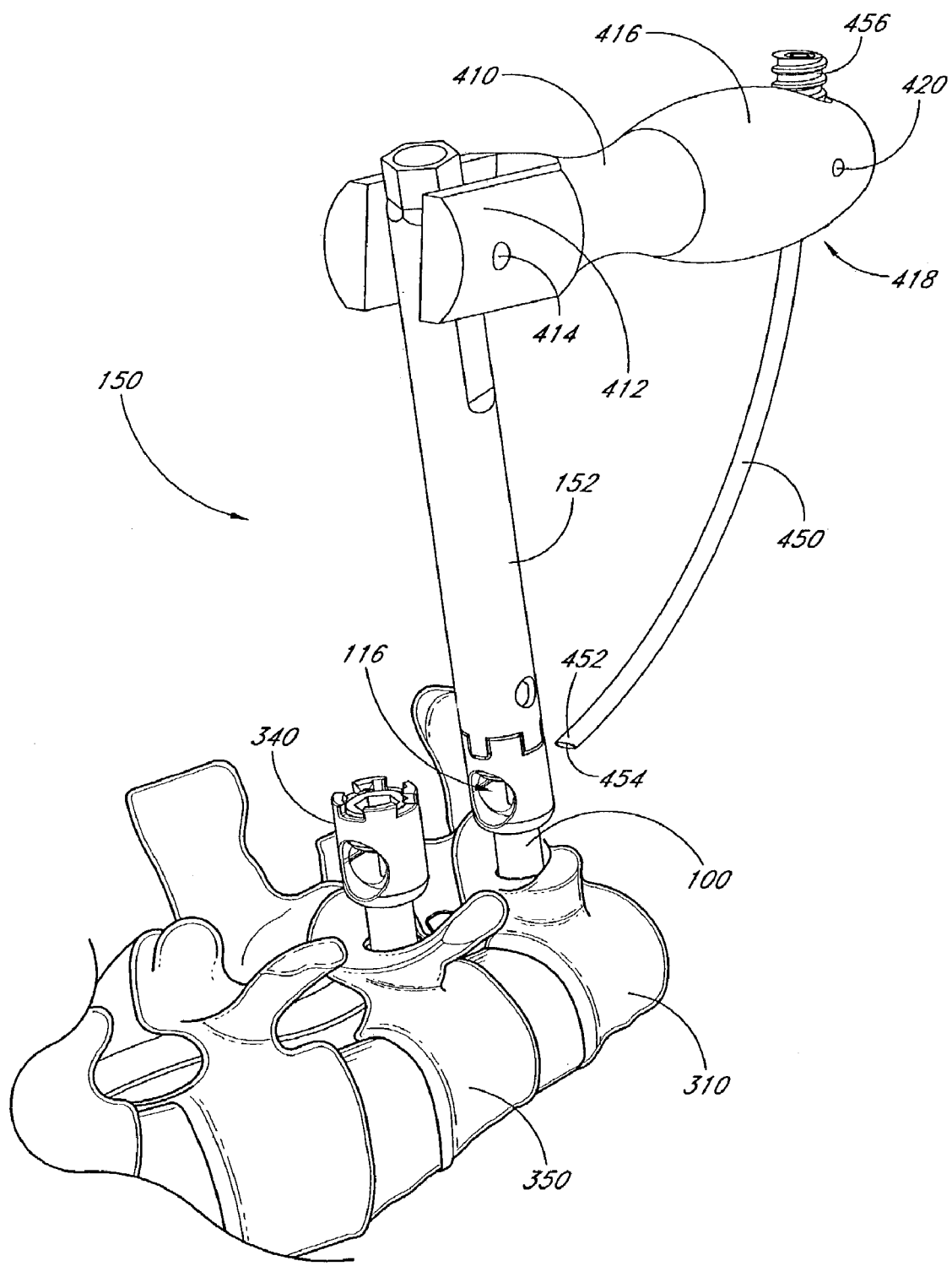
FIG. 33 illustrates an alignment device for positioning a guidewire though a bone anchor in accordance with one aspect of the present invention.

FIG. 33 shows an overview of the guide wire insertion device 400 according to one embodiment of the invention. The guide wire insertion device comprises a handle 410 and a hollow access needle 450. The handle 410 is detachably joined to the outer adapter 152 of the driver 150. The handle 410 is forked at its proximal end 412. Each fork is provided with a pivot pin 414, which engages the pivot hole 153 (FIG. 28) of the outer adapter 152. The forked proximal end 412 of the handle 410 may be spread slightly to allow the pivot pins 414 to engage the pivot hole 153. The handle 410 swings on its pivot pins 414 at the pivot hole 153 of the outer adapter 152 of the driver 150 to insert the access needle 450 through the transverse portal 116 of the bone anchor 100.

A hollow access needle 450 is attached to the distal end 416 of the handle 410. In one embodiment, the access needle 450 is disposed within an opening 418 at the distal end 416 of the handle 410. A screw (not shown) may be threaded through a screw hole 420 at the distal end 416 of the handle 410 to tighten the access needle 450 within the opening 418. The lengthwise position of the access needle 450 within the opening 418 is therefore adjustable to allow the access needle 450 to be aimed through the transverse portal 116 of the bone anchor 100. In one embodiment, the access needle 450 may be aimed such that it passes through the transverse portal 116 at a point lower (towards the threads 102 in FIG. 2) than the center of the transverse portal 116 because obstructions encountered during the in vivo insertion of the access needle 450 may deflect the needle 450 towards the inside of its curvature and the center of the transverse portal 116.

In several embodiments, the sharp, tapered distal end 452 of the access needle 450 terminates at an opening 454. In one embodiment, the access needle 450 is provided with threaded proximal end 456, the purpose of which is described in further detail below.

Figure 34:
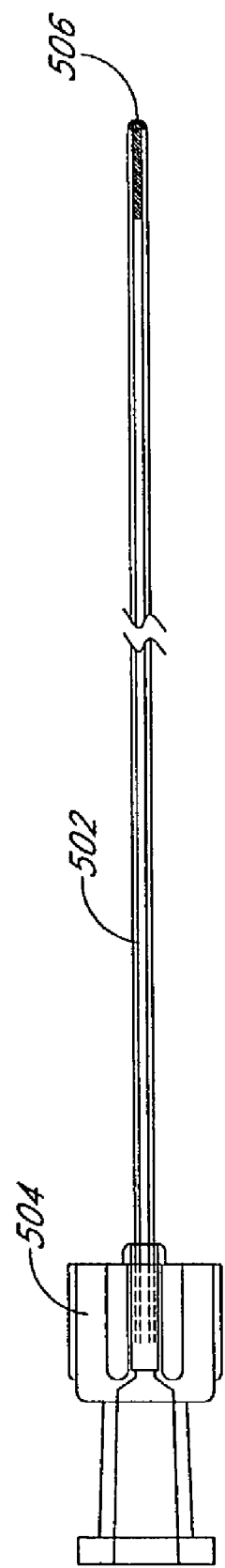
FIG. 34 illustrates a flexible obtuator for positioning within the arcuate arm of the alignment device.

FIG. 34 illustrates a flexible obturator 500 of the guide wire insertion device 400 according to one embodiment. The obturator 500 comprises a tubing 502, a threaded cap 504 on its proximal end and a plug 506 on its distal end. The tubing 502 is sized such that it fits snugly within the hollow access needle 450 and occupies the length of its lumen. The cap 504 can be made with a threaded luer connector which may be tightened onto the threaded proximal end 456 of the access needle 450. The plug 506 may be formed from an adhesive, for example, Loctite 3104, etc. The obturator 500 occupies the lumen of the access needle 450, and minimizes the collection of tissue or other matter within the access needle 450 as it is advanced through the patient.

Figure 35:
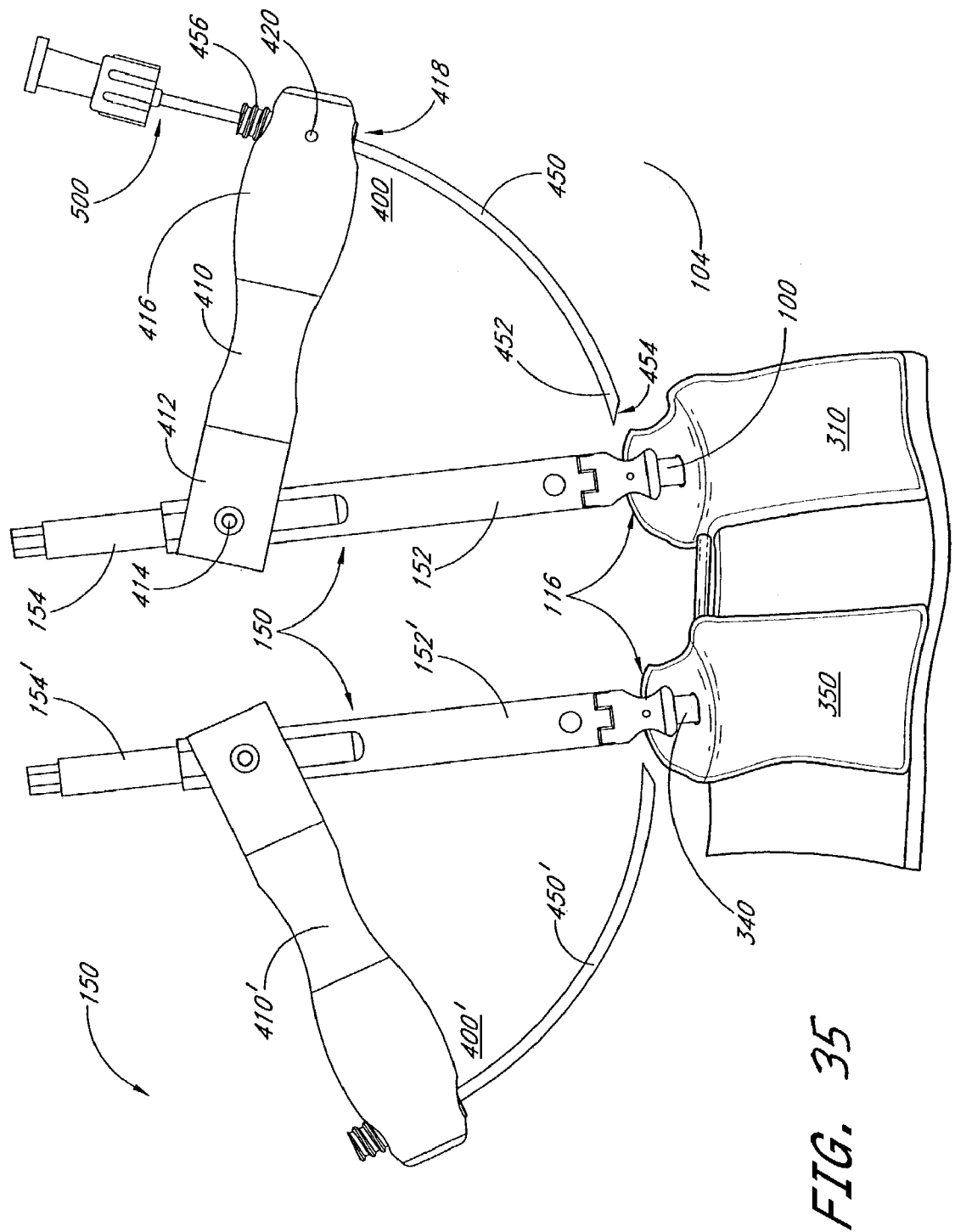
FIG. 35 illustrates a first alignment device coupled to first bone anchor, and a second alignment device coupled to a second bone anchor.

FIG. 35 shows a first guide wire insertion device 400 joined to a first outer adapter 152 engaging a first bone anchor 100 and a second guide wire insertion device 400' joined to the outer adapter 152' engaging a second bone anchor 340. In one embodiment, both handles 410 and 410' are pivoted with respect to outer adapters 152 and 152' to advance access needles 450 and 450' through the patient's tissues and towards the transverse portals 116 of bone anchors 100 and 340, respectively. FIG. 35 also shows an obturator 500 according to one embodiment being inserted into the access needle 450 of the guide wire insertion device 400 as described above with reference to FIG. 34. Preferably, the obturator 500 is inserted into the access needle 450 and threaded onto its threaded proximal end 456 before the access needle 450 is inserted into the patient. Likewise, another obturator 500 may be inserted into the access needle 450'.

Figure 36:
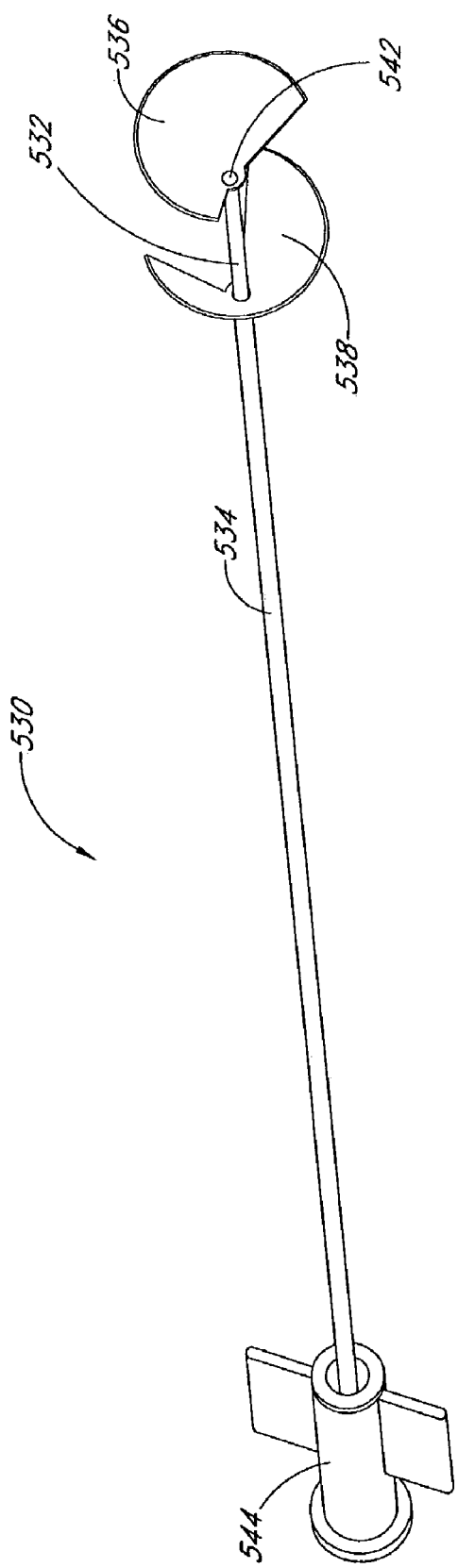
FIGS. 36 and 37 illustrate a guidewire capture device, for positioning within the arcuate arm on an alignment device.
Figure 37:
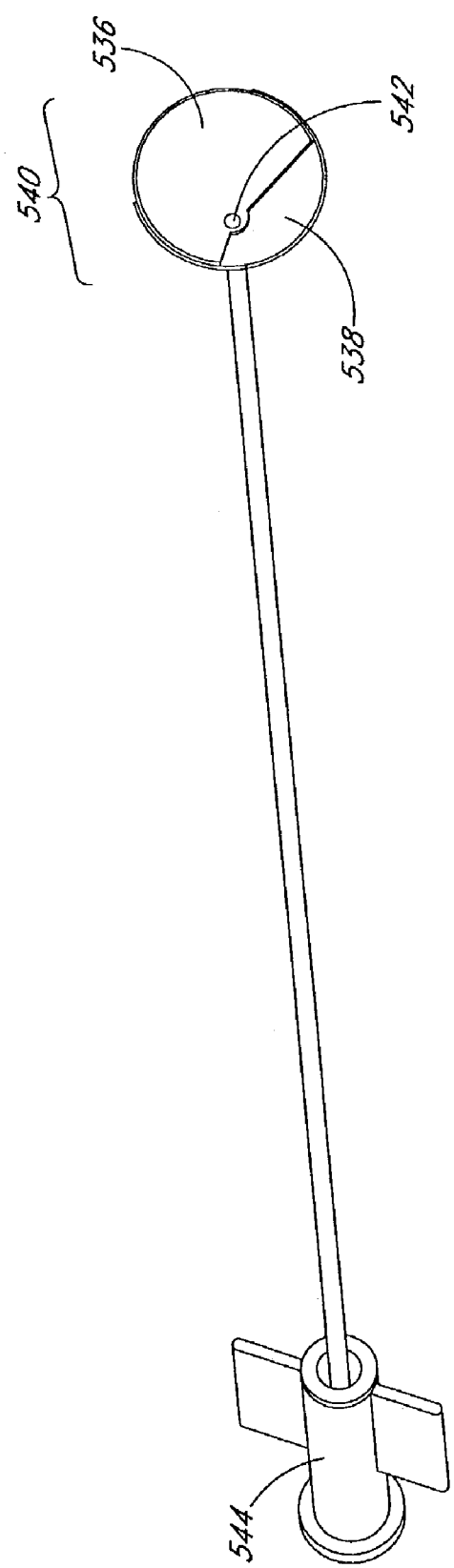

In one embodiment of the present invention, the guide wire insertion device 400 additionally comprises a guide wire snare or capture device 530, illustrated in FIG. 36. The guide wire capture device 530 comprises an inner tubing 532 located coaxially within an outer tubing 534. The inner tubing 532 is provided with an inner half-cone 536 and the outer tubing 534 is provided with an outer half cone 538. The inner half-cone 536 may be furled and retracted within the outer tubing 534. Likewise, the outer half-cone 536 may be furled to ease its insertion into and navigation through the lumen of the hollow access needle 450. Inner half-cone 536 may be rotationally oriented with respect to outer half-cone 538 to form the conical funnel 540 of the guide wire capture device 530, as illustrated in FIG. 37. When a guide wire contacts the conical funnel 540 of the guide wire capture device 530, the guide wire is directed into the lumen 542 of the inner tubing 532. The guide wire capture device 530 also additionally comprises a handle 544 in the illustrated embodiment.

Figure 38:
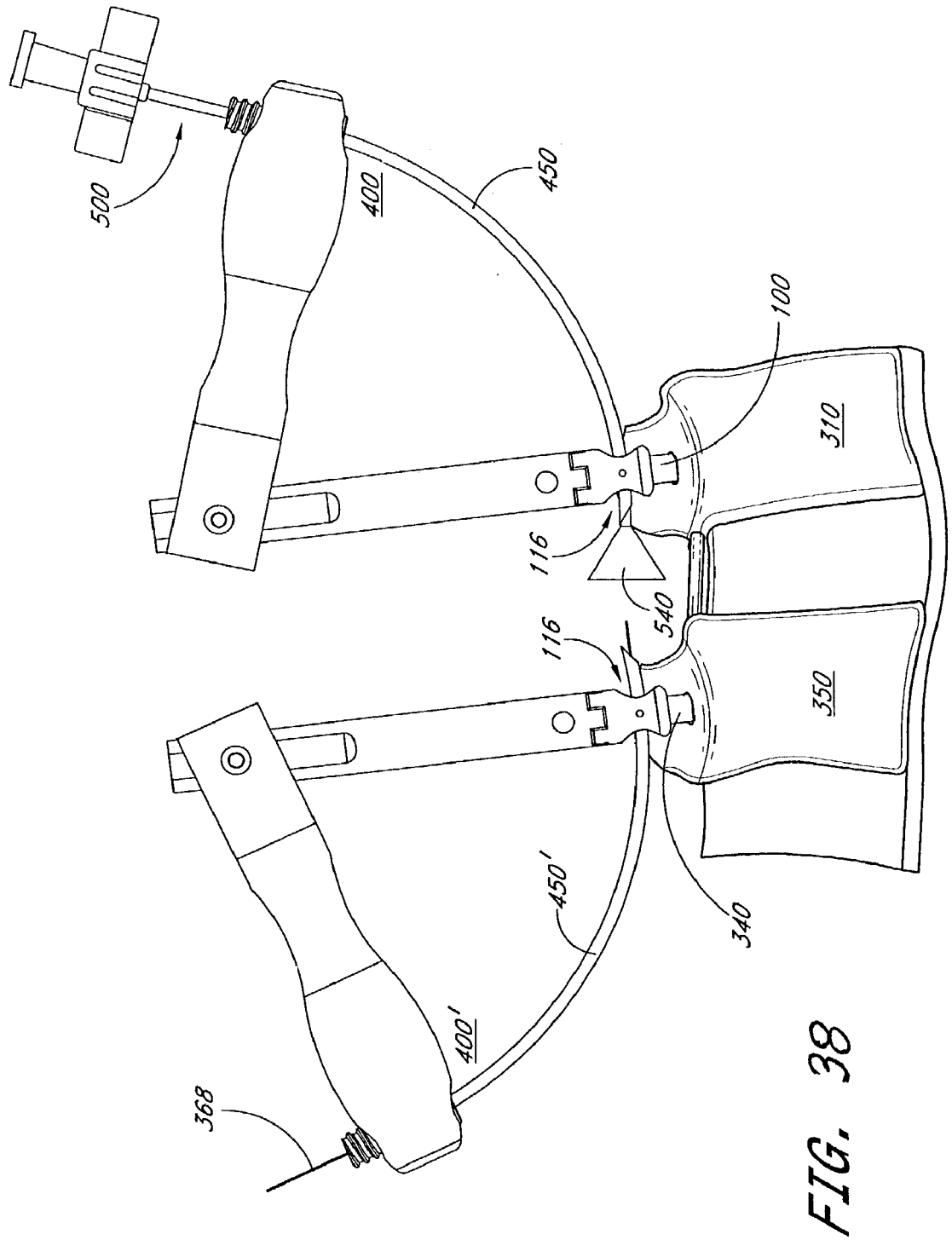
FIG. 38 illustrates the first and second alignment devices, with a guidewire advancing from the first alignment device towards the capture device carried by the second alignment device.

In FIG. 38, the access needle 450 has been advanced through the transverse portal 116 of bone anchor 100, and access needle 450' has been advanced through the transverse portal 116 of bone anchor 340. The guide wire capture device 530 is inserted through the lumen of the access needle 450, and its conical funnel 540 is deployed. A guide wire 368 is inserted through the lumen of the access needle 450' and advanced towards the conical funnel 540 of the guide wire capture device 530. When the guide wire 368 contacts the conical funnel 540, the guide wire 368 is directed into the lumen 542 of the inner tubing 532 of the guide wire capture device 530.

Figure 39:
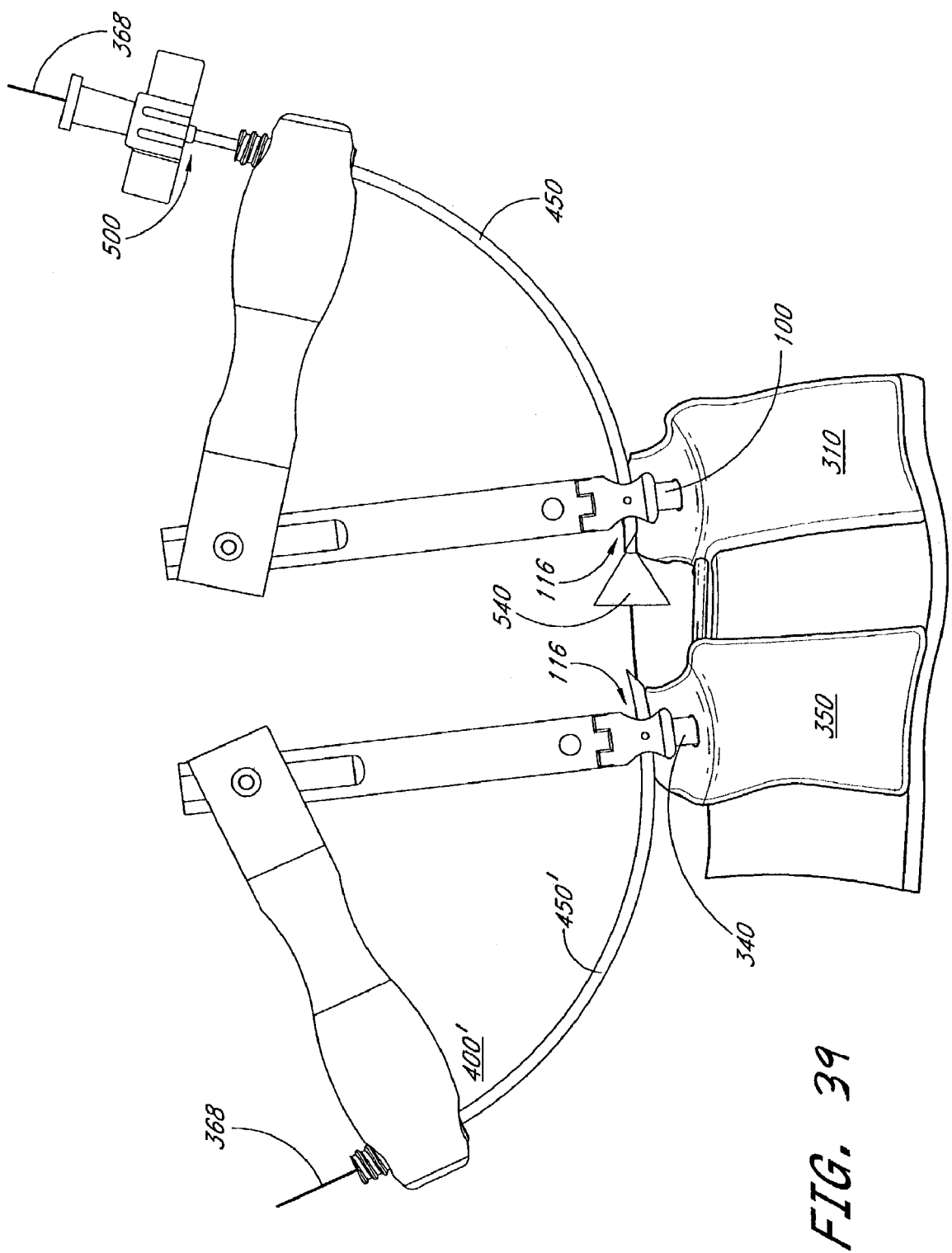
FIG. 39 is an illustration as in FIG. 38, after the guidewire has entered the guidewire capture device and traversed the curved arm on the second alignment device.

In FIG. 39, the guide wire 368 is advanced through the lumen 542 of the inner tubing 532 until it extends past the handle 544 of the guide wire capture device 530. Various methods of inserting guide wires are known in the art and the invention is not limited to the methods disclosed herein. Instead, any method of inserting a guide wire known to those skilled in the art may be used in accordance with the present invention. Following placement of the guide wire 368, the first insertion device 400 and second insertion device 400' may be removed.

A flexible or curved bone drill (not shown) may be advanced along the guide wire 368 to clear a path between the transverse portals 116 of bone anchors 100 and 340. In one embodiment, the bone drill arm carrying the drill bit is provided with a certain degree of flexibility to allow it to travel along the arcuate course of the guide wire 368. In another embodiment, the curvature the bone drill arm carrying the drill bit is matched to the curvature of the linkage rod 200 to ensure that the path cleared between transverse portals 116 of bone anchors 100 and 340 fits the linkage rod 200. The bone drill is removed from the guide wire 368 after a path has been cleared between transverse portals 116 of bone anchors 100 and 340.

Figure 40:
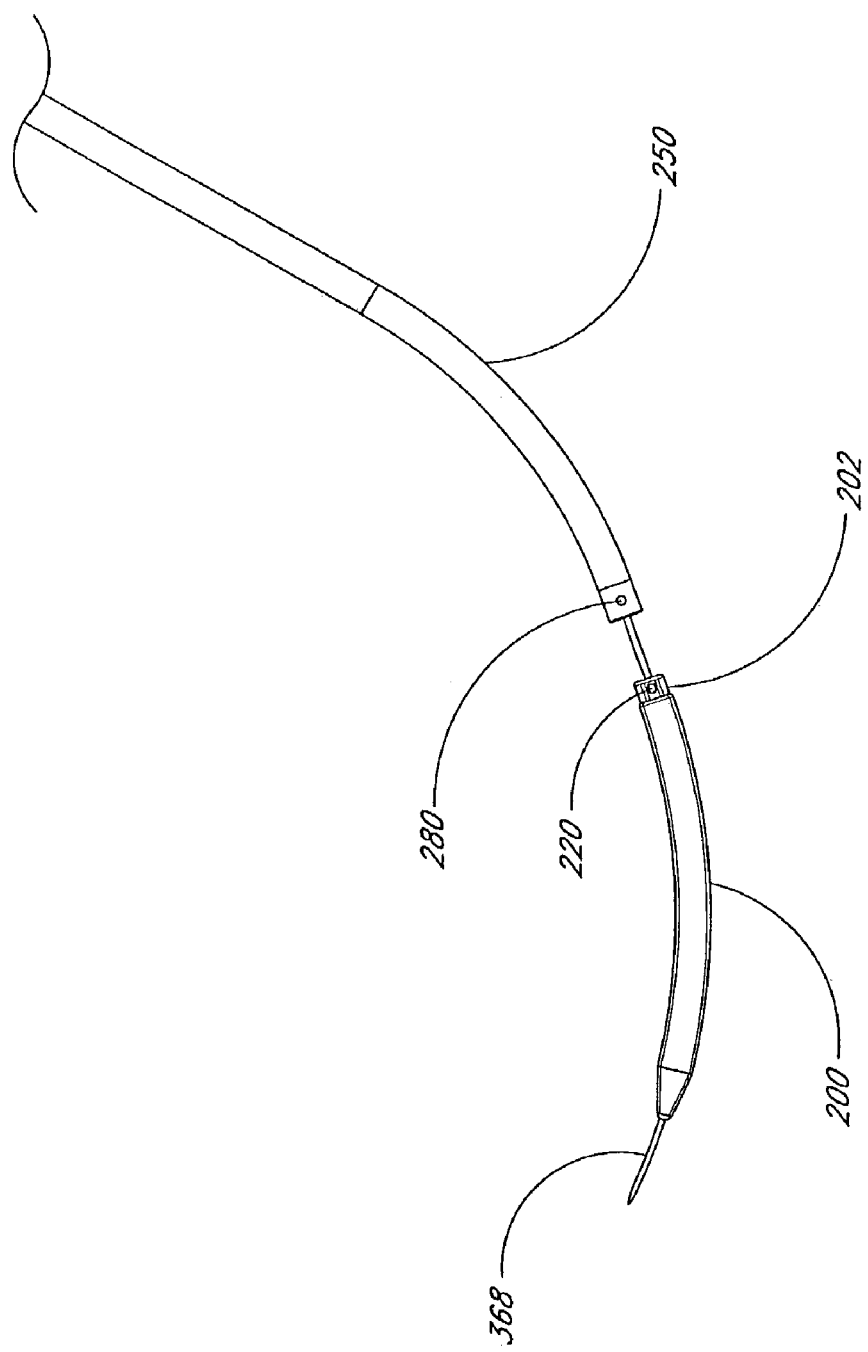
FIG. 40 is a side elevational view of a linkage rod, decoupled from an insertion tool, both over a guidewire.

In FIG. 40, a linkage rod 200 and its insertion tool 250 are shown arranged over the guide wire 368. The linkage rod 200 and insertion tool 250 are described above with reference to FIGS. 4-6. The linkage rod 200 and insertion tool 250 in the embodiment illustrated in FIG. 40 are provided with slightly different indexing features than the linkage rod and insertion tool described with reference to FIGS. 4-6. Referring again to FIG. 40, the linkage rod 200 is provided with one or more bumps 220 on its hexagonal proximal end 202. The bumps 220 are complementary with one or more holes 280 at the distal end of the insertion tool 250. In FIG. 40, the linkage rod 200 is detached from the insertion tool 250. The attachment of the linkage rod 200 to the insertion tool 250 is described above with reference to FIGS. 4-6.

Figure 41:
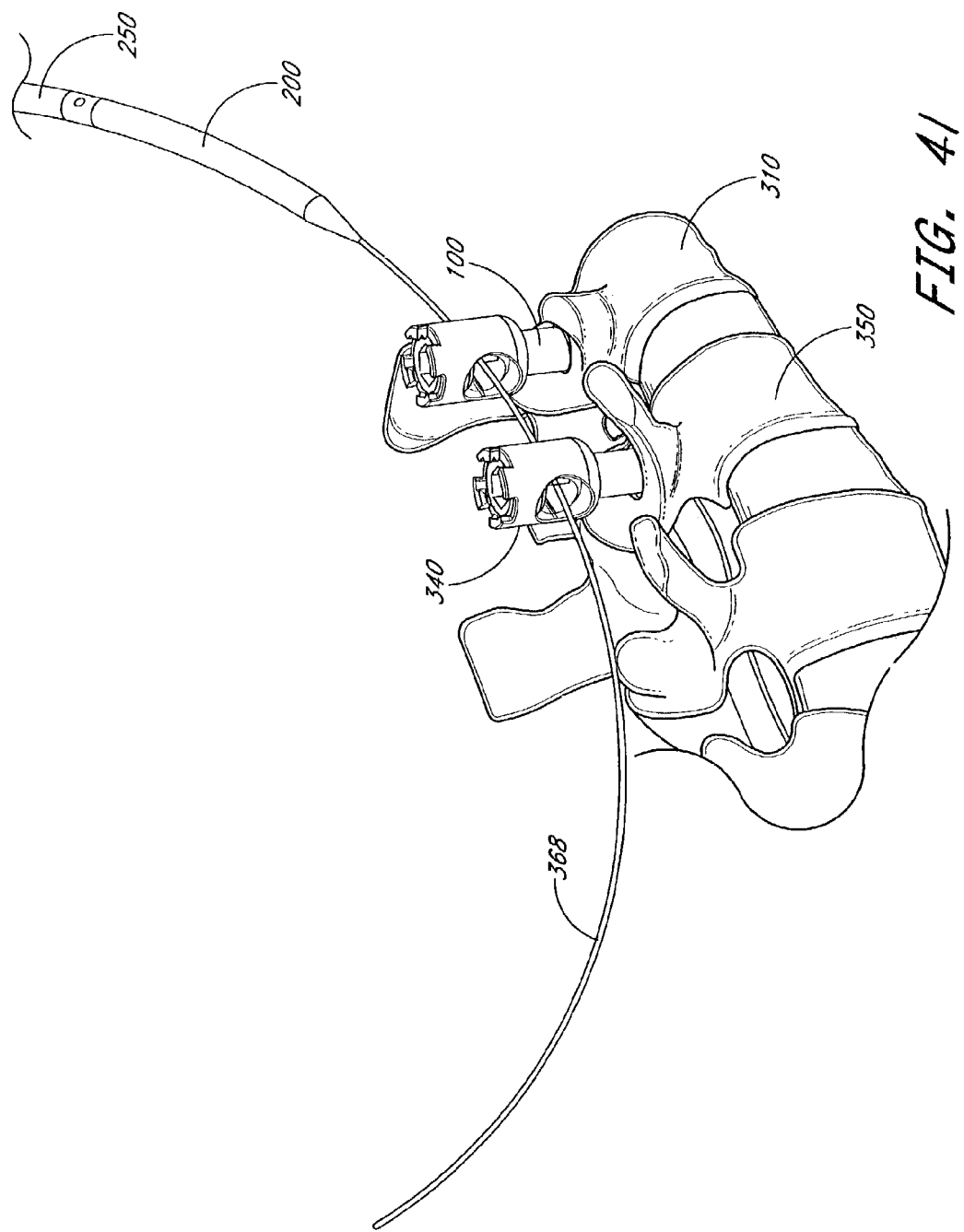
FIG. 41 is an side elevational perspective view of a guidewire positioned through two adjacent bone anchors, and a linkage rod being advanced along the guidewire by an insertion tool.

In FIG. 41, the insertion tool 250 is used to advance the linkage rod 200 over the guide wire 368 towards the bone anchors 100 and 340. While the linkage rod 200 is inserted from a rostral or sacral approach (tail-to-head) in the illustrated embodiment, it may also be inserted from a caudal approach (head-to-tail) in another embodiment.

Figure 42:
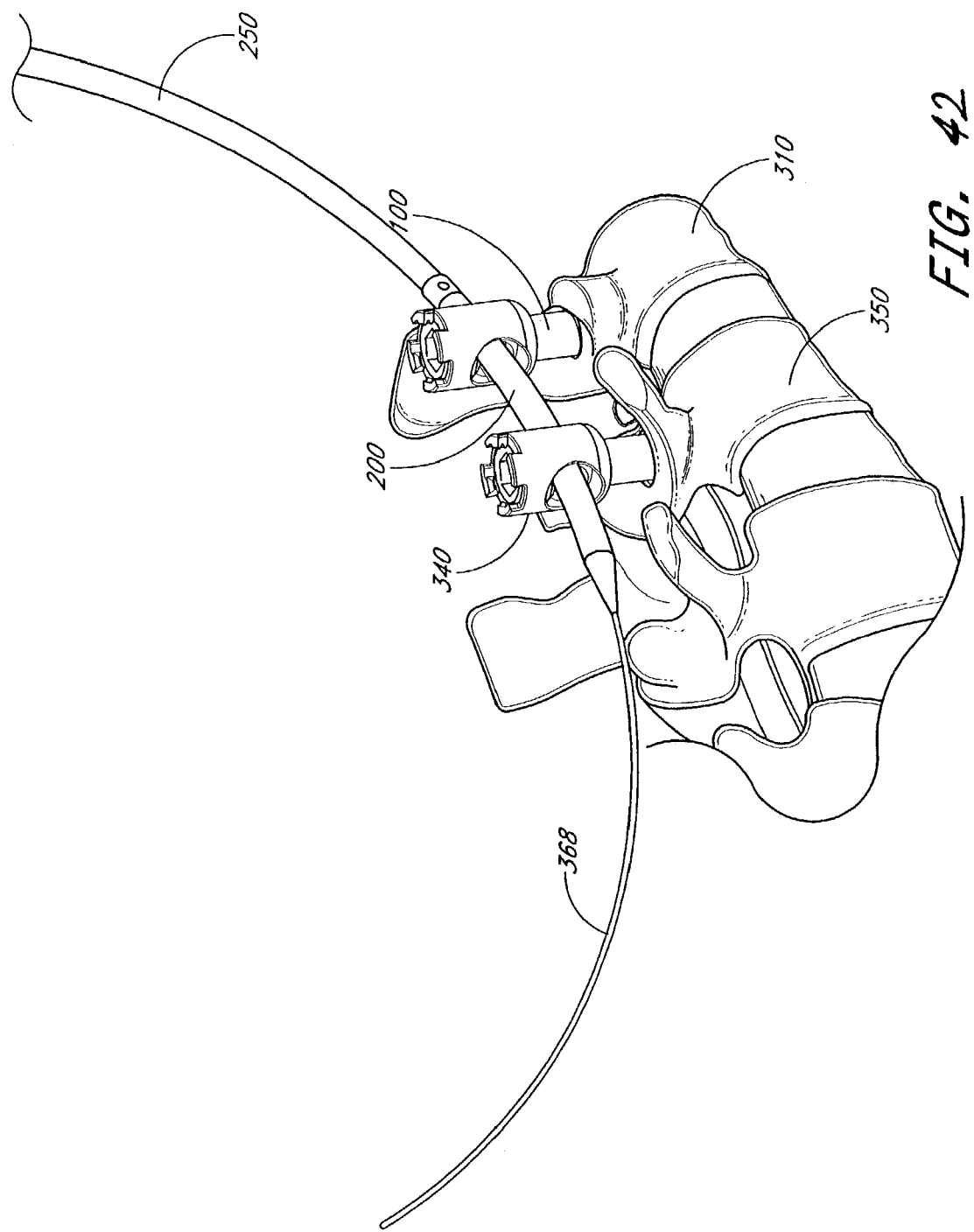
FIG. 42 is an illustration as in FIG. 41, with the linkage rod positioned within the first and second bone anchors.
Figure 43:
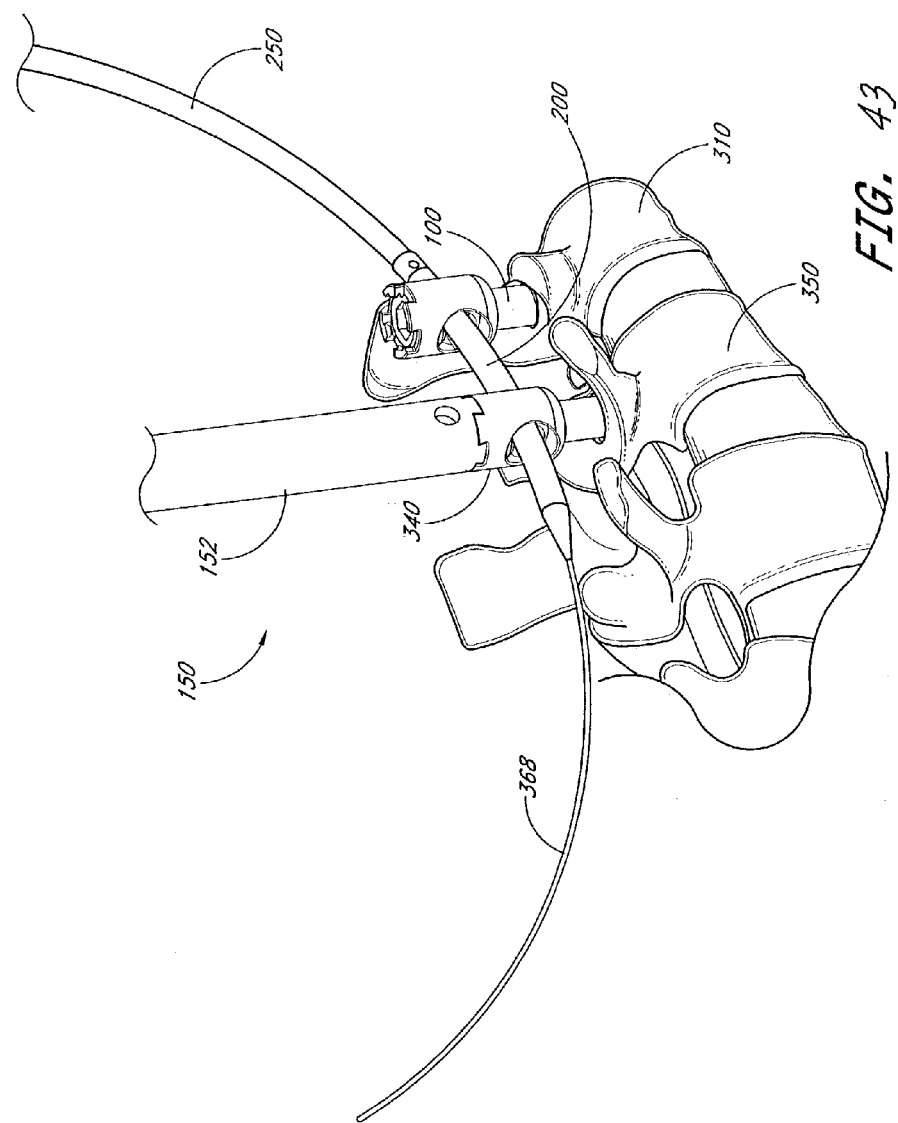
FIG. 43 is an illustration as in FIG. 42, with a driver in position to lock the first bone anchor to the linkage rod.
Figure 44:
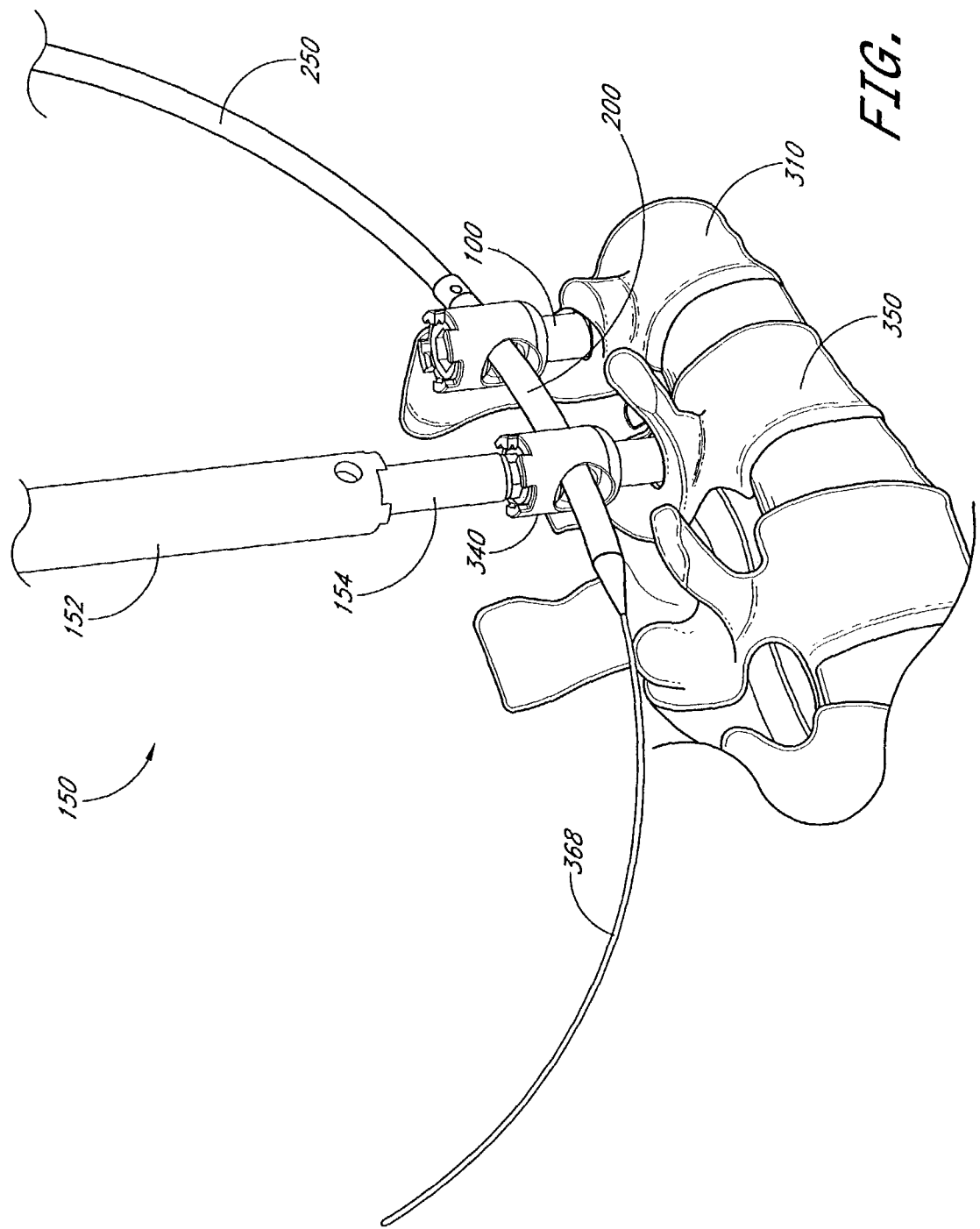
FIG. 44 is an illustration as in FIG. 43, with a portion of the driver tool proximally retracted.

In FIG. 42, the linkage rod 200 is inserted through the respective connectors 104 within bone anchors 100 and 340. The connector 104 within the bone anchor 100 is described above with reference to FIGS. 2-3. In FIGS. 43-44, the inner adapter 154 of the driver 150 is used to tighten the locking cap 106 within the bone anchor 340, fixing the linkage rod 200 within the bone anchor 340, as described above with reference to FIGS. 2-3. The outer adapter 152 of the driver 150 engages the head of bone anchor 340 to prevent it from rotating as the locking cap is tightened. The engagement between the bone anchor 340 and the driver 150 is described above with reference to FIGS. 1-3 in the context of bone anchor 100.

In FIG. 44, the driver 150 (comprising the outer adapter 152 and the inner adapter 154) is withdrawn from the bone anchor 340. The locking cap 106 in the bone anchor 100 is similarly tightened, fixing the linkage rod 200 within the bone anchor 100.

Figure 45:
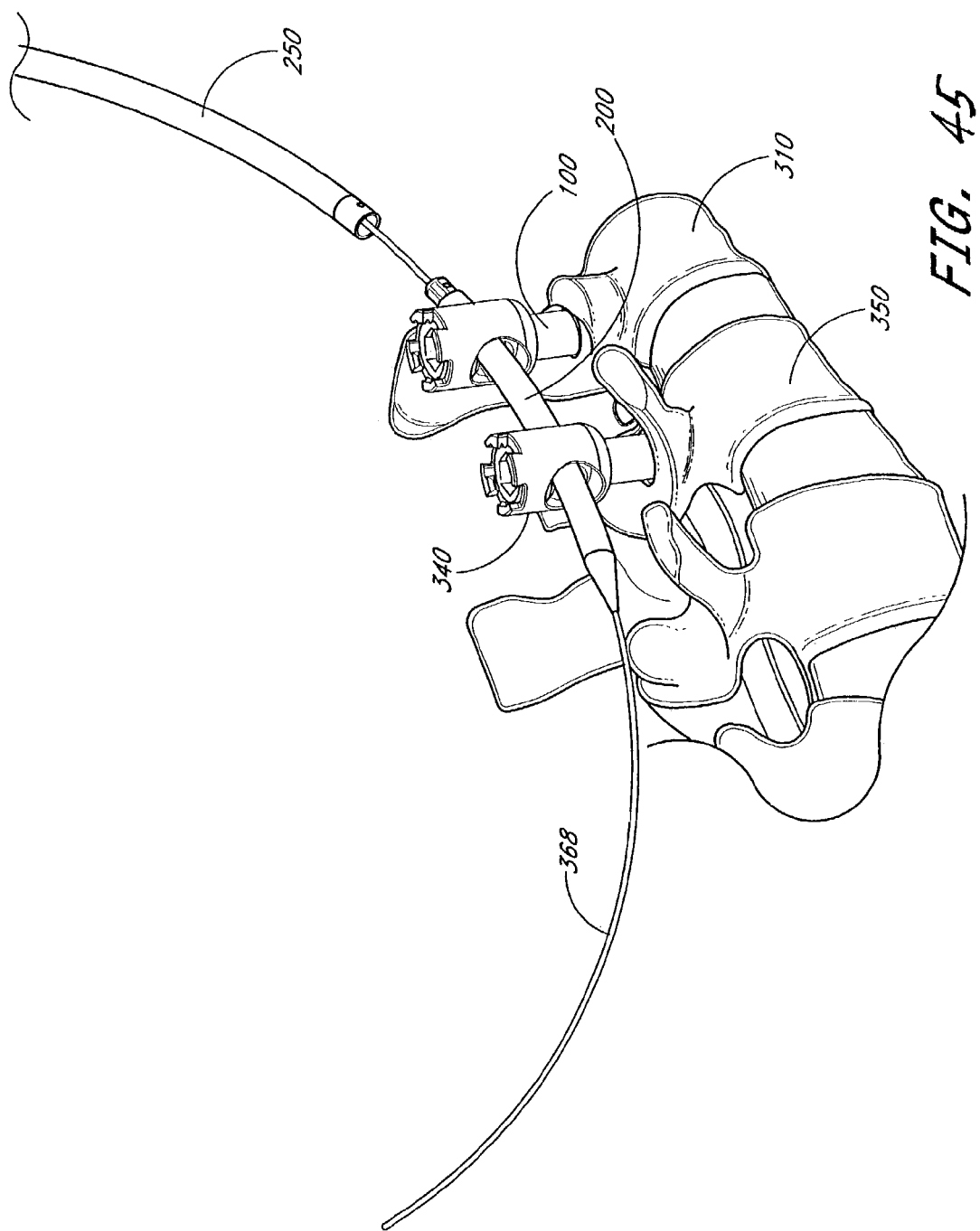
FIG. 45 is an illustration as in FIG. 44, with the driver tool retracted, the first and second bone anchors locked onto the linkage rod, and the insertion tool decoupled from the linkage rod.

In FIG. 45, the insertion tool 250 is released from the linkage rod 200. The attachment and detachment of the linkage rod 200 to and from the insertion tool 250 is discussed above with reference to FIGS. 4-6. Afterwards, the driver 150, the sheath 320 and the guide wire 368 are removed from the patient.

Figure 46:
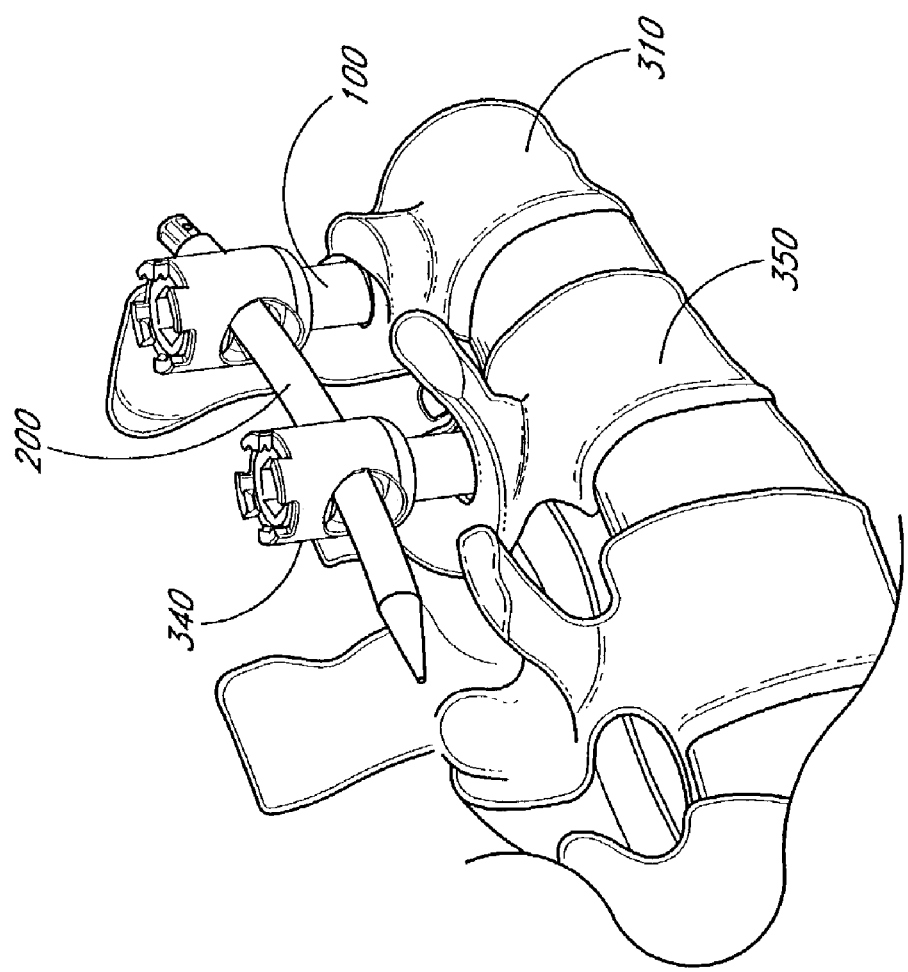
FIG. 46 is an illustration as in FIG. 45, with the insertion tool and the guidewire removed from the linkage rod, illustrating a formed in place one level posterior fusion device in accordance with the present invention.

FIG. 46 illustrates the percutaneously assembled in place prosthesis resulting from the procedure described above, comprising the bone anchors 100, 340 and the linkage rod 200.

Figure 47:
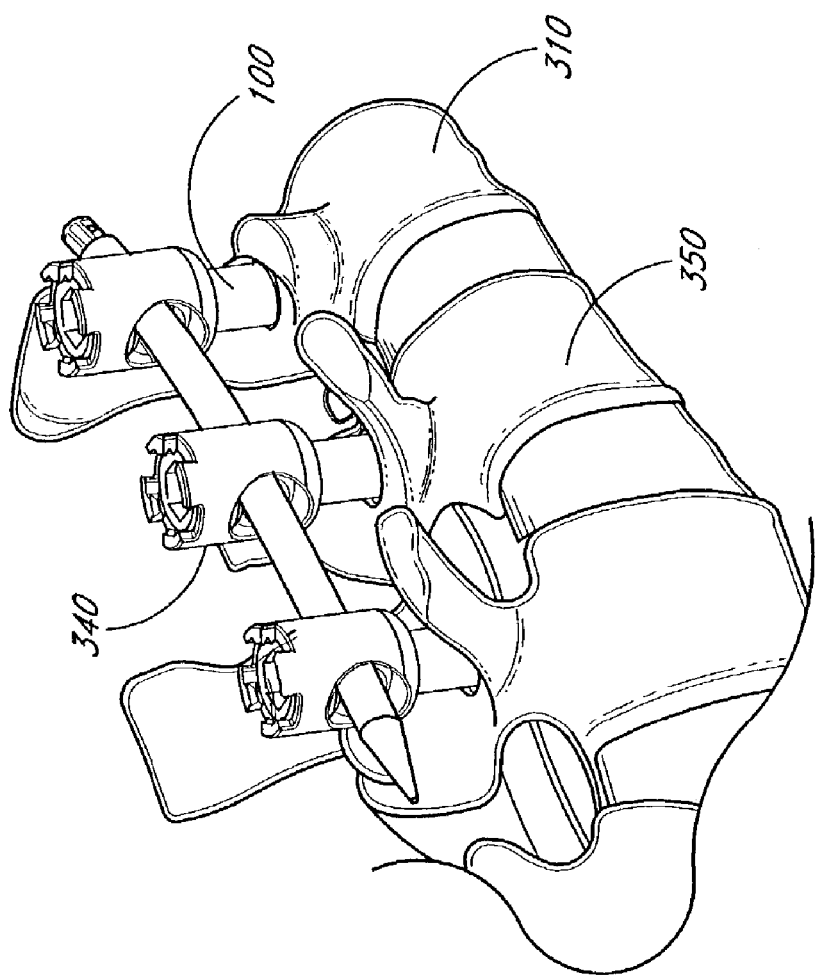
FIG. 47 is an illustration as in FIG. 46, showing a two level fusion or fixation device, percutaneously assembled in accordance with the present invention.

FIG. 47 illustrates a three level prosthesis comprising an additional bone anchor inserted into an additional adjacent vertebral body, to provide a three level spinal fusion.

Figure 48:
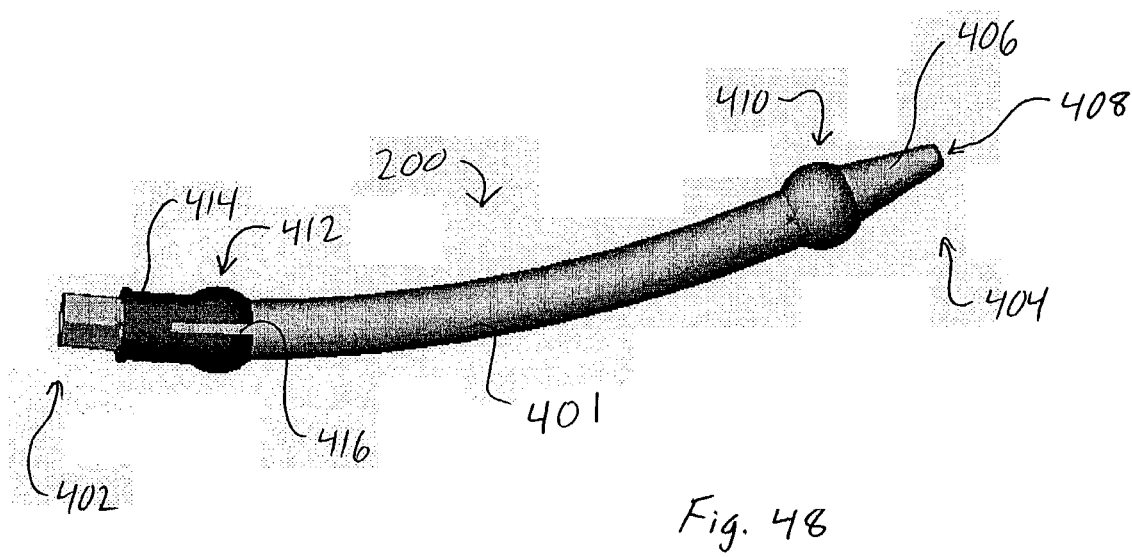
FIG. 48 is a side elevational schematic view of an alternate linkage rod in accordance with the present invention.
Figure 49:
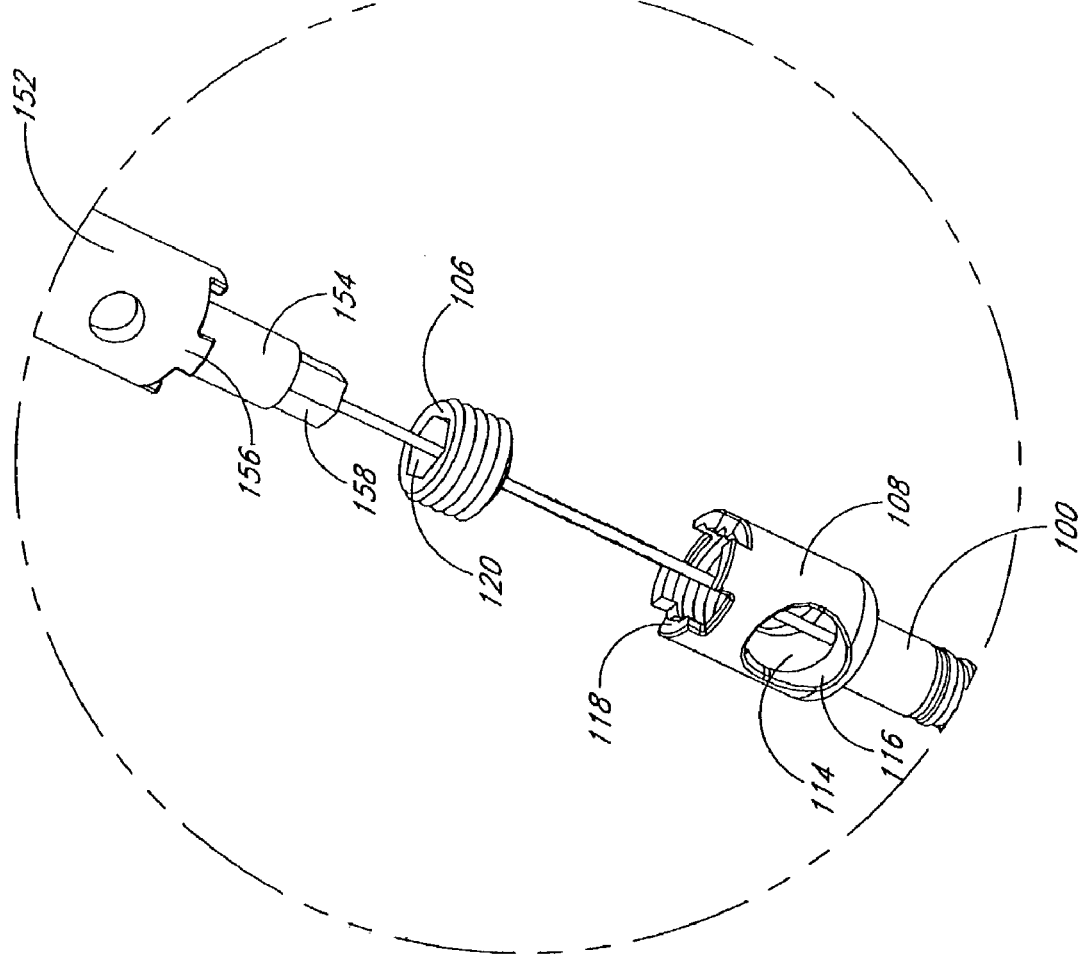
FIG. 49 is an enlarged exploded view as in FIG. 3A, showing the proximal end of a bone anchor adapted for use with the linkage rod of FIG. 48.

Referring to FIGS. 48 and 49, there is illustrated an alternate implementation of the invention. FIG. 48 illustrates a side elevational view of a modified linkage rod 200. Linkage rod 200 in FIG. 48 may be the same general dimensions and configuration as the linkage rods disclosed previously herein, except as described below. In all of the linkage rods disclosed herein, the linkage rod 200 comprises an elongate body 401 extending between a proximal end 402 and a distal end 404. The length of the body 401 in a device intended for use in a human adult one level lumbar or lumbar-sacral fusion, will generally be in the range from about 30 mm to about 90 mm. A linkage rod 200 intended for a two level fusion in the same environment will generally have a length within the range of from about 50 mm to about 110 mm.

In an embodiment of the body 401 having a circular cross sectional configuration, the diameter of the body 401 will generally be in the range of from about 3 mm to about 8 mm. In one embodiment, the diameter of the body 401 in a two level fusion device is about 6.35 mm. In general, the cross sectional area of the body 401, which may be expressed as a diameter in a circular cross sectional implementation, may be varied depending upon the desired structural integrity of the finished implant.

The distal end 404 of the body 401 may be provided with a distal opening 408 to a central guidewire lumen, not illustrated. The distal end 404 may also be provided with tapered tip 406 as has been previously discussed. In general, the tapered tip 406 may facilitate navigation through the tissue tract, as well as introduction of the body 401 into the bone anchor. Tapered tip 406 may be integrally formed with the body 401, or attached thereto in a subsequent manufacturing step.

The body 401 is generally provided with a preformed curve, such that it forms a portion of an arc as illustrated. In certain implementations of the invention, the arc has an approximately constant radius of curvature along the length the body 401. The radius of curvature of body 401 is generally in excess of about 19 cm, and, in many embodiments, within the range of from about 8 cm to about 30 cm. In one implementation of the invention, intended for a two level fusion, the overall length of the body 401 is about 65 mm, the diameter is about 6.35 mm, and the radius of curvature is about 19 cm.

The radius of curvature of the body 401 may be equal or approximately the same as the radius of curvature of the hollow access needle 450 in the guidewire insertion device 400 discussed previously. Thus, the radius may be approximately equal to the distance between the access needle 450 and the pivot point 414, which is also equal to the effective lever arm length of the handle 410. This facilitates introduction of the linkage rod 200 along the same curved tissue tract used by or created by the access needle 450.

The linkage rod 200 illustrated in FIG. 48, unlike the embodiments previously illustrated herein, includes a distinct distal locking surface 410 formed by a discontinuity in the outer profile of the body 401. In the illustrated embodiment the distal locking surface 410 is in the form of an increase in the cross sectional area of the body 401, such as a spherical or curved enlargement of the profile of the body 401. This distal locking surface 410 is adapted to cooperate with a modified bone anchor, illustrated in FIG. 49.

FIG. 49 is an enlarged, explored view of the proximal end of the bone anchor and distal end of a driver tool as illustrated in FIG. 3A, except that the connector 104 has been omitted from the embodiment illustrated in FIG. 49. Instead, the distal locking surface 410 is adapted for insertion through the transverse portal 116 and positioning within the proximal head 108. The locking cap 106 may be threadably distally advanced into the head 108, to compress against the distal locking surface 410 and lock the bone anchor with respect to the linkage rod throughout any of a variety of angular orientations, as had been discussed previously. For this purpose, the distal wall of the chamber within the head 108 may be provided with a complimentary curved surface for cooperating with the distal locking surface 410. Similarly, the distal surface on the locking cap 106 may be concave in the distal direction, to increase the surface area of contact between the locking cap 106 and the distal locking surface 410.

A similar locking configuration may be used in connection with the proximal bone anchor, and the proximal locking surface 412. Proximal locking surface 412 is carried by an axially moveable tubular collar 414. In the illustrated embodiment, the collar 414 comprises a generally tubular body axially movably carried by the body 401 of the linkage rod 200. The proximal locking surface 412 comprises a spherical, semi-spherical, curved or other enlargement in the cross-sectional area collar 414, to provide a locking surface which may be useful throughout a variety of angular orientations as has described. One or two or three or four more axially extending slots 416 may be provided on the proximal lock, to facilitate compression of the lock from a slideable orientation to a locked orientation in which it is compressed against the body 401. In the illustrated embodiment, two or more axially extending slots extend in a proximal direction from the distal end of the lock.

In use, the linkage rod 200 is advanced distally along a guidewire, through a tube, or otherwise through the first and second bone anchors. With the distal locking surface 410 positioned within the proximal head 108 of the distal bone anchor, the locking cap 106 of the distal bone anchor is tightened to lock the linkage rod 200 with respect the distal bone anchor. The proximal lock is thereafter axially distally advanced along the insertion tool and/or linkage rod 200, until the proximal locking surface 412 is positioned within the head 108 of the proximal bone anchor. The locking cap 106 of the proximal bone anchor is tightened, to lock the proximal locking surface 412 against the body 401.

The proximal lock may be distally advanced along the insertion tool and/or linkage rod 200 in any of a variety of manners, such as by distally advancing a pusher sleeve which is axially movably carried on the insertion tool.

In one embodiment, the transverse portal 116 of the proximal bone anchor is provided with a proximal opening having a first diameter and distal opening having a second, smaller diameter. The outside diameter of proximal locking surface 412 is dimensioned relative to the portal 116 such that it can pass through the proximal opening on the transverse portal 116 but cannot pass distally through the distal opening of the transverse portal 116. In this manner, the clinician can perceive tactile feedback once the proximal lock has been distally advanced into position within the head 108. This same construction can be utilized on the distal bone anchor as well, such that distal advancement of the distal locking surface 410 may be accomplished until the positive stop is felt by the clinician as the distal locking surface 410 is seated within the head 108. The driver tool can be provided with indicium of the rotational position of the bone anchor.

In all of the foregoing embodiments, the insertion tool may be provided with a curved distal region, having a radius of curvature which approximates the radius of curvature of the linkage rod, described above. Thus, in one embodiment both the linkage rod 200 and the distal portion of the insertion tool are provided with a curve having a radius of approximately 12 cm. This further facilitates introduction of the linkage rod and insertion tool along a curved tissue tract, while minimizing trauma to surrounding tissue, as the linkage rod 200 is navigated through the first and second bone anchors.

The foregoing construction also allows the percutaneous access site for the introduction of the linkage rod 200 to be predetermined distance from the longitudinal axis of the driver 150. For example, in one implementation of the guidance system, the radius of curvature of the curved needle 450 is approximately 9 cm. This enables the percutaneous access site to be approximately 8 centimeters from the percutaneous entry site for the driver 150. The transdermal access site for the linkage rod is preferably no more than about one radius away from the driver 150. This allows minimization of the length of the tissue tract, and thus minimizes the access induced trauma to surrounding tissue.

Not all of the steps described above are critical to the minimally invasive implantation of posterior fixation hardware. Accordingly, some of the described steps may be omitted or performed in an order different from that disclosed. Further, additional steps may be contemplated by those skilled in the art in view of the disclosure herein, without departing from the scope of the present invention.

The present inventors contemplate the interchangeability of and recombination of various structural and method elements in the foregoing description. For example, the guidewire may be positioned through portals of adjacent bone anchors utilizing either the procedures disclosed in the copending patent applications previously incorporated by reference herein. Alternatively, the guidewire may be positioned utilizing the pivotable guidance system disclosed herein. As a further alternative, a tubular sleeve may be advanced over the guidewire and through the portals on bone anchors 100, with the guidewire thereafter removed. The linkage rod 200 may thereafter be advanced through the tubular sleeve.

The linkage rod 200 may be advanced utilizing the manual insertion tool 250, as disclosed herein. Alternatively, the linkage rod 200 may be releasably connected to the distal end of a curved pivotable arm 450, using releasable connection structures disclosed elsewhere herein. In this manner, the pivotable insertion system such as that illustrated in FIG. 33 can be utilized to insert the linkage rod 200 through one or more apertures 116 in one or more bone anchors 100.

The various materials, methods and techniques described above provide a number of ways to carry out the invention. Of course, it is to be understood that not necessarily all objectives or advantages described may be achieved in accordance with any particular embodiment described herein. Thus, for example, those skilled in the art will recognize that the components of the system may be made and the methods may be performed in a manner that achieves or optimizes one advan-

What is claimed is:

1. A method of implanting spinal fusion hardware, comprising the steps of:
   positioning a first bone anchor, having a first aperture, in a first vertebral body;
   positioning a second bone anchor, having a second aperture, in a second vertebral body;
   mounting an alignment tool to at least one bone anchor, the alignment tool comprising a curved guide needle;
   advancing the guide needle through at least one of the first and second apertures; and
   advancing a guide wire through the first and second apertures; wherein at least a portion of the alignment tool is mounted to the bone anchor before the positioning of a bone anchor step.

2. A method of implanting spinal fusion hardware as in claim 1, wherein the first and second vertebral bodies are adjacent vertebral bodies.

3. A method of implanting spinal fusion hardware as in claim 1, wherein the first and second vertebral bodies are separated by a third vertebral body.

4. A method of implanting spinal fusion hardware as in claim 1, wherein the mounting an alignment tool comprises mounting a central arm on the bone anchor, the central arm pivotably attached to a radial arm, and the guide needle is carried by the radial arm.

5. A method of implanting spinal fusion hardware as in claim 4 wherein the guide needle has a radius of curvature within the range of from about 6 cm to about 15 cm.

6. A method of implanting spinal fusion hardware as in claim 1, additionally comprising the step of advancing a fixation device along the guide wire.

7. A method of implanting spinal fusion hardware as in claim 6, wherein the advancing a fixation device step comprises advancing an inflatable fixation device.

8. A method of implanting spinal fusion hardware as in claim 6, wherein the advancing a fixation device step comprises advancing a preformed, rigid fixation device.

9. A method of implanting spinal fusion hardware as in claim 1, additionally comprising the step of advancing a guide tube along the guide wire and through the first and second apertures.

10. A method of implanting spinal fusion hardware as in claim 9, additionally comprising the step of advancing a fixation device through the guide tube.

11. A method of treating a spine, comprising the steps of: positioning a first bone anchor, having a first aperture, in a first vertebral body; positioning a second bone anchor, having a second aperture, in a second vertebral body; aligning a first guide tube with the first aperture; aligning a second guide tube with the second aperture; and advancing a guide wire through the first tube and into the second tube.

12. A method of treating a spine as in claim 11, further comprising the step of removing the first and second guide tubes, leaving the guide wire extending through the first and second apertures.

13. A method of treating a spine as in claim 12, further comprising the step of advancing an implant along the guide wire and through the first and second apertures.

14. A method of treating a spine as in claim 11, wherein the aligning a first guide tube step comprises advancing a curved guide tube along an arc through tissue in the direction of the first aperture.

15. A minimally invasive method of positioning posterior instrumentation, comprising the steps of:
   positioning a first bone anchor in a first vertebral body;
   positioning a second bone anchor in a second vertebral body;
   advancing a guidewire through a tissue tract to the first bone anchor;
   deflecting the guidewire in between the first and second bone anchors; and
   advancing the guidewire to the second bone anchor;
   wherein the advancing a guidewire through a tissue tract to the first bone anchor step comprises advancing the guidewire through a first curved guide tube,
   wherein the advancing the guidewire to the second bone anchor step comprises advancing the guidewire through a second curved guide tube.

16. A minimally invasive method of positioning posterior instrumentation as in claim 15, wherein the deflecting step comprises deflecting the guidewire along a deflection surface carried by one of the first and second guide tubes.

17. A minimally invasive method of positioning posterior instrumentation as in claim 16, further comprising the step of removing the first and second guide tubes, leaving the guide wire extending through the tissue tract to the first and second bone anchors.

18. A method of performing a one level spinal fixation, comprising the steps of:
   positioning a first bone anchor in a first vertebral body;
   positioning a second bone anchor in a second vertebral body;
   attaching a guidewire placement device to at least one of the first and second bone anchors;
   advancing a wire guide through tissue and into alignment with an aperture on at least one of the bone anchors, by pivoting the wire guide about a pivot point carried by the guidewire placement device;
   advancing a guidewire through the wire guide and through an aperture on each of the first and second bone anchors; and
   advancing a fixation rod along the guidewire and through each of the apertures.

19. A method of performing a one level spinal fixation as in claim 18, wherein at least one of the first and second vertebral bodies is a lumbar vertebral body.

20. A method of performing a one level spinal fixation as in claim 18, wherein at least one of the first and second vertebral bodies is a sacral vertebral body.

21. A method of performing a one level spinal fixation as in claim 18, wherein at least one of the first and second vertebral bodies is a cervical vertebral body.

* * * * *